US009125995B2

(12) United States Patent
Bartlett, II et al.

(10) Patent No.: US 9,125,995 B2
(45) Date of Patent: Sep. 8, 2015

(54) RECONSTITUTION DEVICES

(71) Applicant: GLUCAGO, LLC, El Segundo, CA (US)

(72) Inventors: Rush L. Bartlett, II, Mountain View, CA (US); Peter M. Greco, Jr., Palo Alto, CA (US); Barry J. Davignon, Terre Haute, IN (US)

(73) Assignee: GlucaGo LLC, El Segundo, CA (US)

( * ) Notice: Subject to any disclaimer, the term of this patent is extended or adjusted under 35 U.S.C. 154(b) by 0 days.

(21) Appl. No.: 14/095,801

(22) Filed: Dec. 3, 2013

(65) Prior Publication Data

US 2014/0163465 A1 Jun. 12, 2014

Related U.S. Application Data

(60) Provisional application No. 61/733,647, filed on Dec. 5, 2012.

(51) Int. Cl.
*A61M 5/315* (2006.01)
*A61M 5/19* (2006.01)
*A61M 5/28* (2006.01)

(52) U.S. Cl.
CPC ........... *A61M 5/31596* (2013.01); *A61M 5/286* (2013.01); *A61M 5/31511* (2013.01);
(Continued)

(58) Field of Classification Search
CPC ............ A61M 5/31596; A61M 5/286; A61M 5/31513; A61M 5/31511; A61M 5/19; A61M 2205/0266; A61M 2005/31598; A61M 2205/0216
USPC .................................. 604/82, 89, 90, 91, 191
See application file for complete search history.

(56) References Cited

U.S. PATENT DOCUMENTS 2,591,706 A 4/1952 Lockhart
2,869,543 A 1/1959 Ratcliff et al.
(Continued)

FOREIGN PATENT DOCUMENTS

DE 1291859 4/1969
EP 0112574 7/1984
(Continued)

OTHER PUBLICATIONS

Oct. 22, 2013 International Search Report for PCT/US2013/038490 issued by the European Patent Office as Searching Authority, Oct. 22, 2013 pp. 1-7.
(Continued)

*Primary Examiner* — Manuel Mendez
(74) *Attorney, Agent, or Firm* — Dorsey & Whitney LLP

(57) ABSTRACT

A one-part reconstitution device is described, for temporarily separating two substances into two compartments within a cartridge or syringe and allowing for mixture of the two substances within the cartridge or syringe. In various embodiments, the one-part reconstitution device may include an outer, contact portion configured to contact an inner surface of the cartridge or syringe, and an inner, deflection portion positioned within the contact portion. The deflection portion may be movable from a locked position, in which the deflection portion causes the contact portion to exert a first radial force against the inner surface, to an unlocked position, in which the deflection portion causes the contact portion to exert a second radial force against the inner surface. The second radial force may be less than the first radial force, and the contact portion and the deflection portion may comprise one part.

20 Claims, 54 Drawing Sheets

(52) U.S. Cl.
CPC .............. *A61M5/31513* (2013.01); *A61M 5/19* (2013.01); *A61M 5/284* (2013.01); *A61M 2005/31598* (2013.01); *A61M 2205/0216* (2013.01); *A61M 2205/0266* (2013.01)

(56) References Cited

U.S. PATENT DOCUMENTS

| | | | |
|---|---|---|---|
| 3,380,451 | A | 4/1968 | Porter et al. |
| 3,678,931 | A | 7/1972 | Cohen |
| 3,699,961 | A | 10/1972 | Szpur |
| 3,785,379 | A | 1/1974 | Cohen |
| 3,838,689 | A | 10/1974 | Cohen |
| 3,885,710 | A | 5/1975 | Cohen |
| 3,939,833 | A | 2/1976 | Hansson et al. |
| 4,031,892 | A | 6/1977 | Hurschman |
| 4,059,109 | A * | 11/1977 | Tischlinger ............... 604/88 |
| 4,061,144 | A | 12/1977 | Strickman et al. |
| 4,215,701 | A * | 8/1980 | Raitto ............... 600/576 |
| 4,715,854 | A | 12/1987 | Vaillancourt |
| 4,921,491 | A | 5/1990 | Champ |
| 5,279,606 | A | 1/1994 | Haber et al. |
| 5,352,196 | A | 10/1994 | Haber et al. |
| 5,377,689 | A | 1/1995 | Mercereau |
| 5,433,705 | A | 7/1995 | Giebel et al. |
| 5,562,631 | A | 10/1996 | Bogert |
| 5,620,423 | A * | 4/1997 | Eykmann et al. ............ 604/219 |
| 5,630,796 | A | 5/1997 | Bellhouse et al. |
| 5,752,940 | A | 5/1998 | Grimard |
| 5,779,668 | A | 7/1998 | Grabenkort |
| 5,785,683 | A | 7/1998 | Szapiro et al. |
| 5,817,055 | A | 10/1998 | Ljungquist |
| 5,971,953 | A | 10/1999 | Bachynsky |
| 6,001,080 | A | 12/1999 | Kuracina et al. |
| 6,001,089 | A | 12/1999 | Burroughs et al. |
| 6,602,223 | B2 | 8/2003 | Szapiro et al. |
| 2002/0168530 | A1 | 11/2002 | Tingey et al. |
| 2003/0100921 | A1 | 5/2003 | Addis et al. |
| 2004/0186432 | A1 | 9/2004 | Barry et al. |
| 2006/0178638 | A1 | 8/2006 | Reynolds |
| 2008/0234654 | A1 | 9/2008 | McCarthy et al. |
| 2008/0319400 | A1 | 12/2008 | Thorne, Jr. et al. |
| 2009/0036864 | A1 | 2/2009 | Moy et al. |
| 2009/0062740 | A1 | 3/2009 | Thorne |
| 2009/0247957 | A1 | 10/2009 | Heutschi |
| 2009/0254035 | A1 | 10/2009 | Kohlbrenner et al. |
| 2010/0168712 | A1 | 7/2010 | Tuckwell et al. |
| 2011/0106021 | A1 | 5/2011 | Ruegg et al. |
| 2012/0209171 | A1 | 8/2012 | Vedrine et al. |
| 2013/0226081 | A1 | 8/2013 | Davies et al. |

FOREIGN PATENT DOCUMENTS

| | | |
|---|---|---|
| EP | 0340899 A2 | 11/1989 |
| EP | 0511402 A1 | 11/1992 |
| JP | 09-225032 | 9/1997 |
| WO | 2007/131013 | 11/2007 |
| WO | 2010/139793 | 12/2010 |

OTHER PUBLICATIONS

Oct. 8, 2013 International Search Report for PCT/US2013/047935 issued by the Korean Patent Office as Searching Authority, Oct. 8, 2013 pp. 1-3.

Oct. 8, 2013 Written Opinion for PCT/US2013/047935 issued by the Korean Patent Office as Searching Authority, Oct. 8, 2013, pp. 1-8.

Mar. 19, 2013 International Search Report for PCT/US2012/056318 issued by the Korean Patent Office as Search Authority, Mar. 19, 2013 pp. 1-3.

Jun. 9, 2011 International Search Report for PCT/US2011/030910 issued by the United States Patent Office as Search Authority, Jun. 9, 2011 pp. 1-2.

* cited by examiner

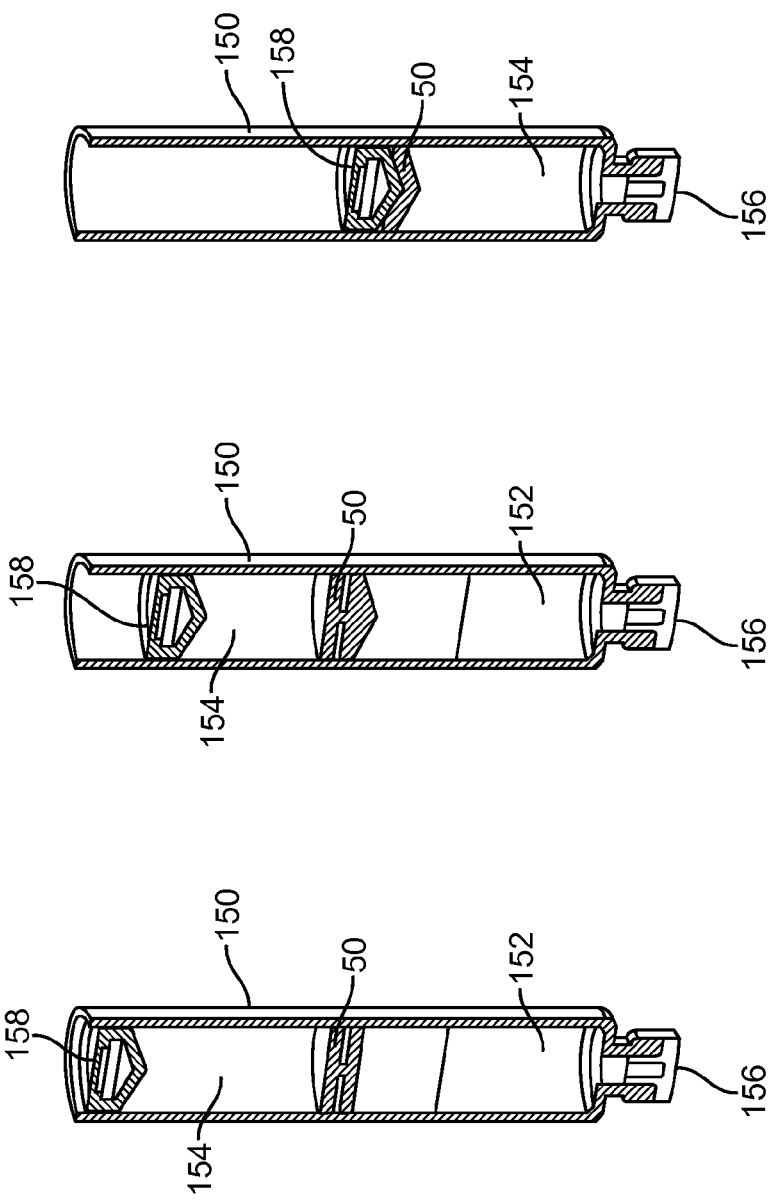

RECONSTITUTION DEVICES

CROSS-REFERENCE TO RELATED APPLICATION

This application claims priority to U.S. Provisional Patent Application No. 61/733,647, filed on Dec. 5, 2012, which is hereby fully incorporated by reference.

BACKGROUND

Lyophilized, spray-dried, or solid medicines that are injected generally require dissolution into a liquid in order to be injected. This process of mixing a solid with a liquid to produce an injectable form of a medication is commonly termed reconstitution. Reconstitution may also refer to mixing of any combination of liquids, solids, and gas components, whether pharmaceutically active, an expedient, or an inert carrier material. Approximately one third of all injected medicines are reconstituted prior to use. These medicines include, but are not limited to, vaccines, basic materials, acidic materials, diluents, buffers, proteins, peptides, monoclonal antibodies, antibodies, fragments of biological material, antigens, organics, inorganics, DNA, RNA, liposomes, nanoparticles, small molecules, large molecules, atomic or molecular materials, combinations of any of these, and many other substances and combinations.

The two main drawbacks of current techniques for reconstitution of injectable medications are that they are either difficult to use, expensive and/or cumbersome to manufacture, or both. Some reconstitution systems contain a bypass channel within the wall of the cartridge or syringe housing that allows liquid to flow through from one compartment to another. This requires a custom piece of glass or plastic in the form of a cartridge or syringe, which is typically expensive and difficult to produce. Additionally, the rubber component used to separate dry and liquid materials in the two compartments of such a bypass syringe are often prone to slipping when force is applied in one chamber. This slippage may cause premature leakage around the rubber component and/or the bypass.

Therefore, although a variety of reconstitution devices have been developed, improvements would still be desirable. Ideally, an improved reconstitution device would provide consistent and reliable separation of a two different substances in two separate compartments of a cartridge or syringe, with very little tendency for leakage from one compartment to the other or unwanted slipping of the reconstitution device. Also ideally, such a reconstitution device would be relatively easy and inexpensive to manufacture. At least some of these objectives will be met by the embodiments described herein.

SUMMARY OF THE DISCLOSURE

The various embodiments of reconstitution devices described below facilitate mixing and/or reconstitution of two or more materials. The reconstitution devices generally include a plunger (or plunger-like device, which may be referred to herein as a "barrier," "barrier device," or "reconstitution device") that fits inside a cartridge and/or syringe, nearly or entirely forms a seal with an inner wall of the cartridge and/or syringe to form two compartments when in a first configuration (or "fixed state"), and then activates to a second configuration (or "activated state") to allow for at least partial mixing of substances from the two compartments. The primary mechanism for activation of the reconstitution device may include a variety of actions, including but not limited to unrolling, flipping, dislodging, and/or shrinking of the material under pressure, such that the force(s) causing the seal with the inner wall of the cartridge or syringe are reduced in the activated state as compared to the loaded or fixed state.

The disclosed reconstitution devices facilitate separation and then mixing of multiple components in cartridges and/or syringes. In various embodiments, the components may be two liquids, a solid and a liquid, a solid and a gas, two gases, or any combination thereof. Examples of liquids may include, but are not limited to, lidocaine, epinephrine, phosphate buffered saline, carbonate, bicarbonate, sodium bicarbonate, liquid stable insulin, liquid stable vaccine, water, diagnostic contrast agent, nutritional material, and any other medically relevant liquid.

The various embodiments of a reconstitution device described herein generally operate by changing their shape from a first configuration to a second configuration to allow a substance from one compartment of a cartridge or syringe to pass through and/or around the device into a second compartment. In some embodiments, the reconstitution device/barrier may form one or more flow channels or bypass chambers through which the substance may pass. To facilitate this opening between the two compartments, the barrier or components thereof are often flexible enough to flex, roll, bend, twist, rotate, flip, compress, unplug, pop, squeeze, or the like, to allow one or more flow channels to form through and/or around the barrier, regardless of the diameter of the surrounding cartridge and/or syringe.

In some embodiments, the inner wall of a cartridge and/or syringe may have a different diameter along one portion of its length compared to another portion, thus forming a bump or ring to impede the movement downward of the barrier upon activation until a stronger force than the initial activation force is applied to pop it through the constriction in diameter. In other embodiments, the barrier material may have ridges, guides, pegs, hooks, kinks, or other features/structures that facilitate an increase in friction against the wall after or during the completion of the activation process, such that the flow channels may form without a large movement of the barrier material down the cylindrical housing.

Some versions may unroll, have multiple folds, or include other features, in the loaded state, that that will be undone, moved, popped, or displaced during activation, to allow for the formation of one or more flow channels. According to various embodiments, one or more flow channels may be formed in the center, off-center, around the outside, and/or on the side of the barrier component. The material composing the barrier components may be stacked in alignment under direct connection or separate in order to facilitate a stronger seal between two compartments or additional seals between more than two compartments in series.

Generally, the reconstitution devices described herein allow for reconstitution of two or more components when a force is applied against the reconstitution device. In various embodiments, this force may include pressure, gravity, outside mechanical intervention or movement by a person or device, or any other suitable force.

In one aspect, a one-part reconstitution device for temporarily separating two substances into two compartments within a cartridge or syringe and allowing for mixture of the two substances within the cartridge or syringe may include: an outer, contact portion configured to contact an inner surface of the cartridge or syringe; and an inner, deflection portion positioned within the contact portion. The deflection portion may be movable from a locked position, in which the deflection portion causes the contact portion to exert a first radial force against the inner surface, to an unlocked position, in which the deflection portion causes the contact portion to exert a second radial force against the inner surface. In various embodiments, the second radial force may be less than the first radial force. Additionally, in some embodiments, the contact portion and the deflection portion may be one part.

In some embodiments, the cartridge or syringe may define a longitudinal axis, and the deflection portion may be configured to deflect in a distal direction along the longitudinal axis to move from the locked position to the unlocked position in response to pressure applied to a fluid in the cartridge or syringe proximal to the deflection portion. In some embodiments, the contact portion may include an elastomeric ring. Optionally, the deflection portion may take the form of an elastomeric, dome-shaped portion within the ring. In other embodiments, the deflection portion may have a domed shape, regardless of whether or not the contact portion includes an elastomeric ring.

In some embodiments, the deflection may change from a convex shape to a concave shape upon moving from the locked position to the unlocked position. In some embodiments, an outer diameter of the contact portion is larger in the locked position than in the unlocked position. Some embodiments may further include a plug attached to at least one of the contact portion or the deflection portion, the deflection portion may include a hole, and the hole may be plugged by the plug when the deflection portion is in the locked position and open and not plugged by the plug when the deflection portion is in the unlocked position. In some embodiments, the inner portion, the outer portion and the plug may be one part. Some embodiments may optionally include an outer ring attached to the contact portion, where the deflection portion in the locked position biases the outer ring against the cartridge or syringe, and where the deflection portion in the unlocked position radially retracts the outer ring.

In another aspect, a system for temporarily separating two substances within a syringe and allowing for mixture of the two substances within the syringe may include a syringe and a one-part reconstitution device configured to fit in the syringe. The reconstitution device may include: an outer, contact portion configured to contact an inner surface of the cartridge or syringe; and an inner, deflection portion positioned within the contact portion. The deflection portion may be movable from a locked position, in which the deflection portion causes the contact portion to exert a first radial force against the inner surface, to an unlocked position, in which the deflection portion causes the contact portion to exert a second radial force against the inner surface. The second radial force may be less than the first radial force, and the outer portion and the inner portion may comprise one part.

In some embodiments, the deflection portion may be configured to move from the locked position to the unlocked position without the reconstitution device moving through the syringe. In some embodiments, the deflection portion may be configured to move from the locked position to the unlocked position while a plug of the reconstitution device remains stationary. In some embodiments, the syringe may have a proximal end and a distal end, and the deflection portion may be configured to deflect in a distal direction, relative to the syringe, to move from the locked position to the unlocked position in response to pressure applied to a fluid in the syringe proximal to the deflection portion. In some embodiments, the deflection portion may have a domed shape.

Optionally, the system may further include a plunger driver configured to axially advance within the syringe, where the plunger driver is configured to urge the deflection portion from the locked position to the unlocked position. In some embodiments, the plunger driver may be further configured to axially advance the reconstitution device longitudinally through the syringe. the reconstitution device further comprises a plug attached to at least one of the contact portion or the deflection portion, wherein the deflection portion includes a hole, wherein the hole is plugged by the plug when the deflection portion is in the locked position, and wherein the hole is open and not plugged by the plug when the deflection portion is in the unlocked position.

These and other aspects and embodiments are described in further detail below, in relation to the attached drawing figures.

BRIEF DESCRIPTION OF DRAWINGS

FIGS. 10A-10C are perspective views of a syringe with a one-part reconstitution device, illustrating operation of the reconstitution device, according to another alternative embodiment;

Figure 1:
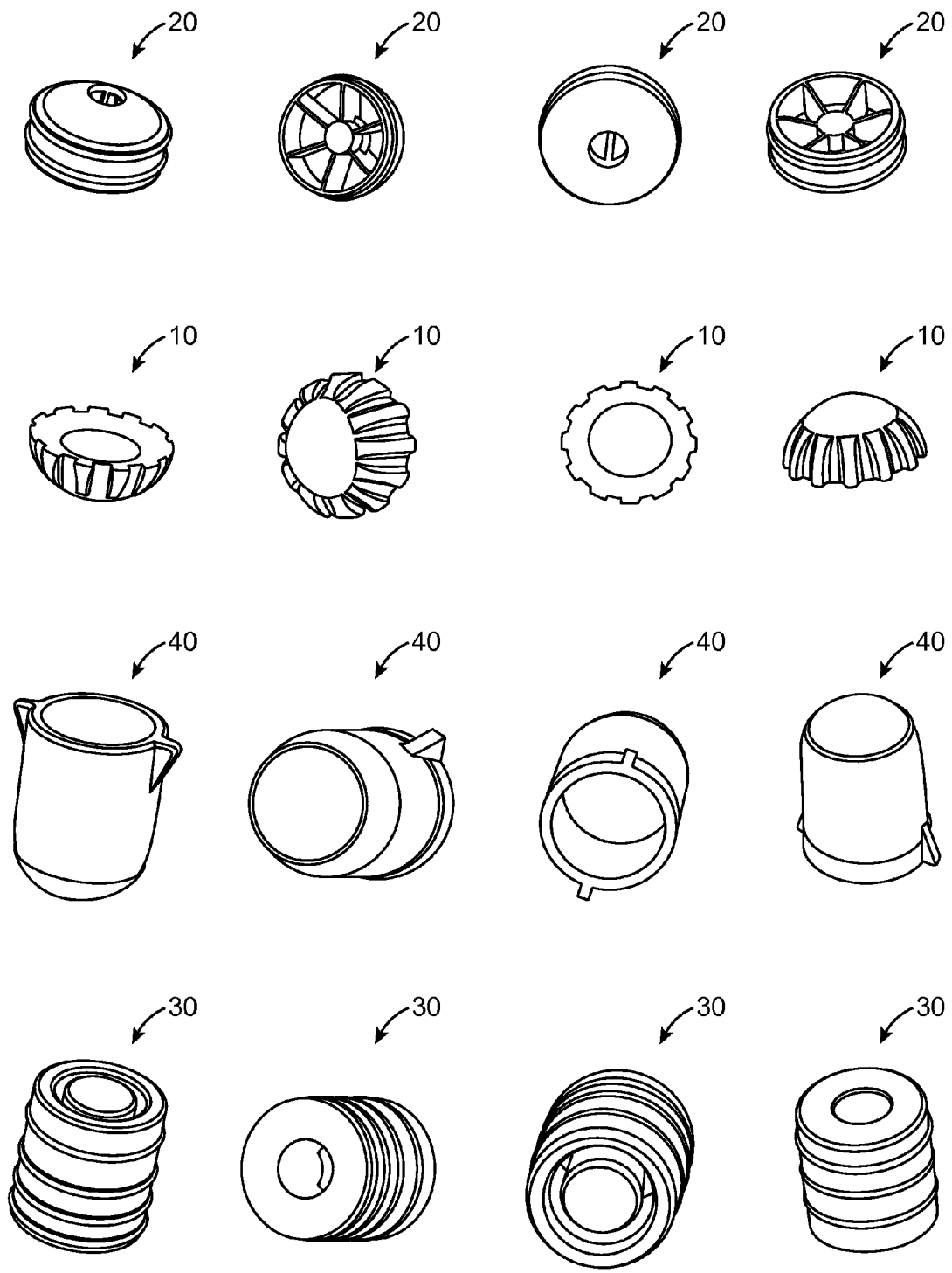
FIG. 1 are various views of several alternative embodiments of a one-part reconstitution device.
Figure 2A:
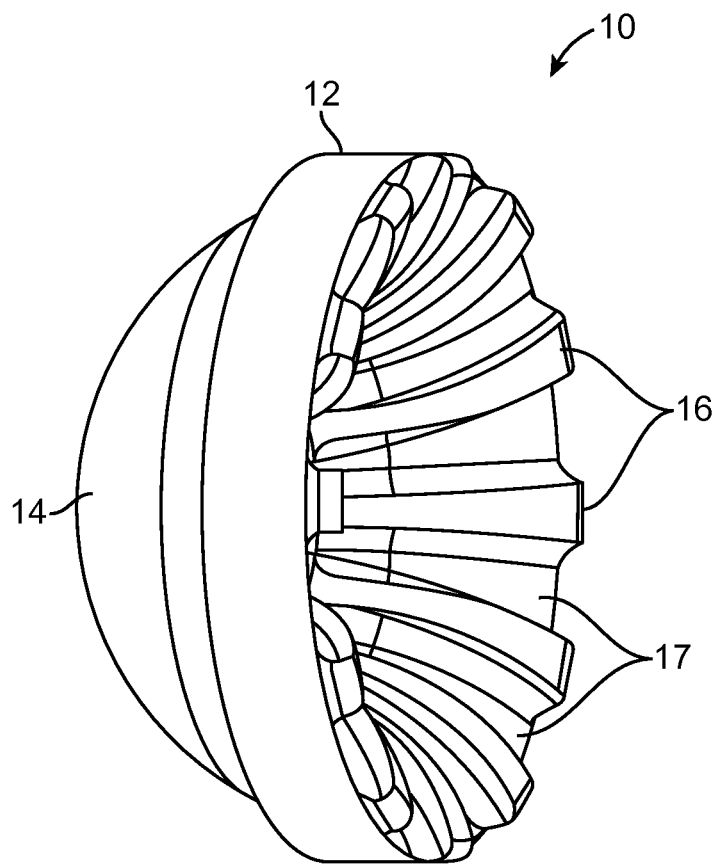
FIGS. 2A-2L are various views of a one-part reconstitution device having a flipping mechanism of action, according to one embodiment.
Figure 2B:
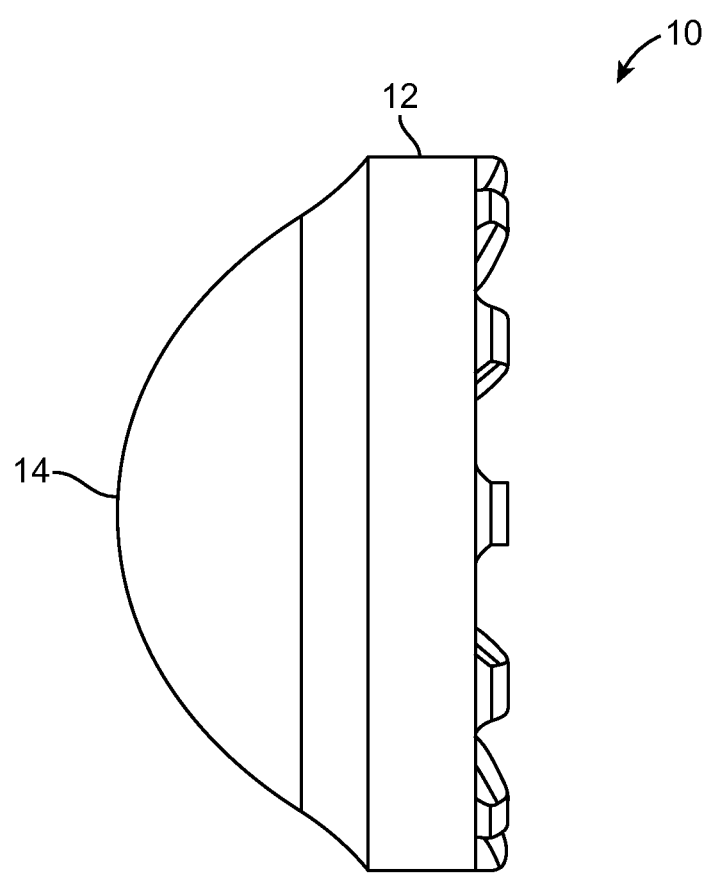
Figure 2C:
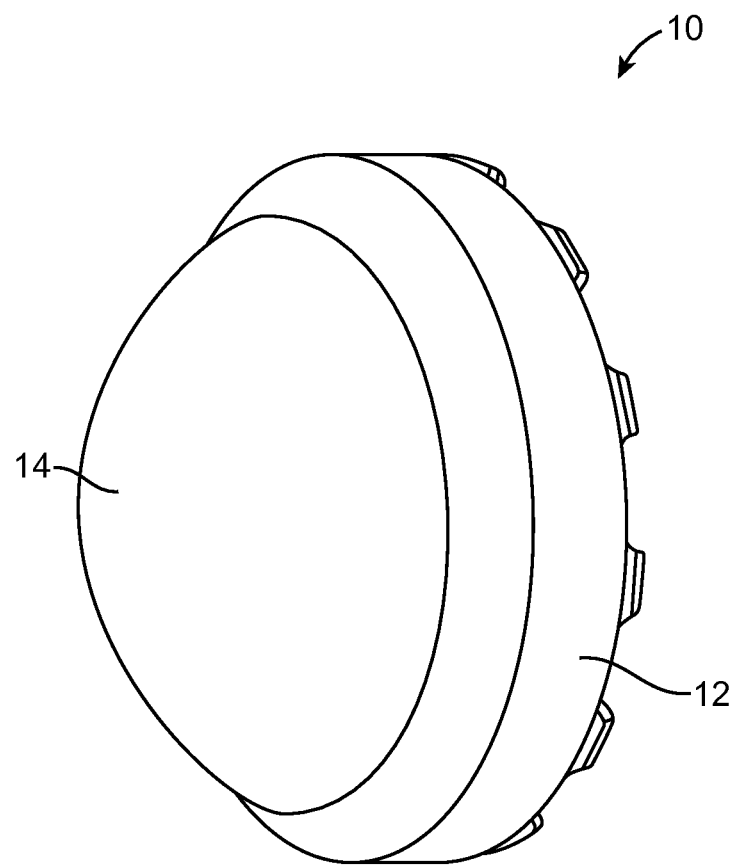
Figure 2D:
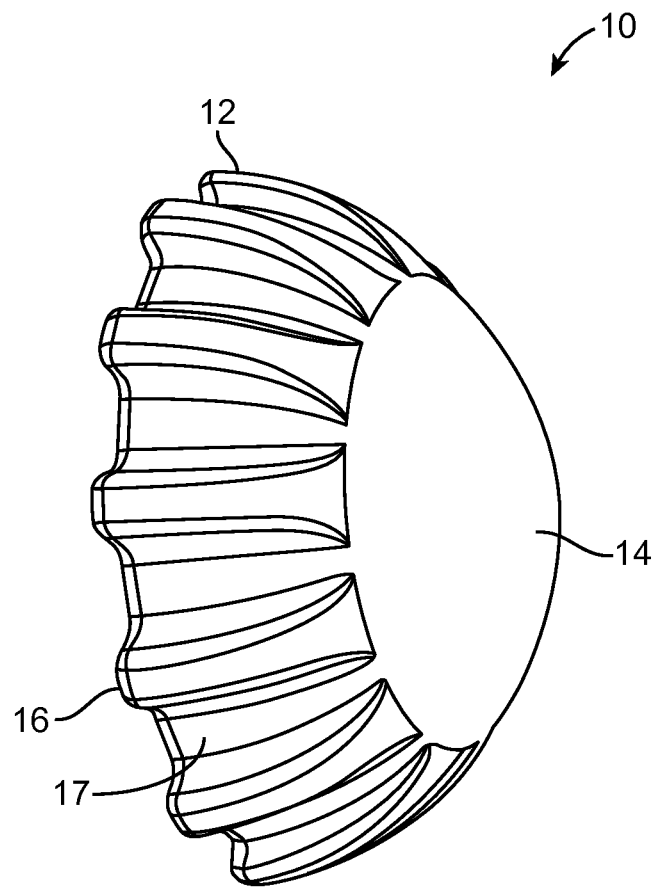
Figure 2E:
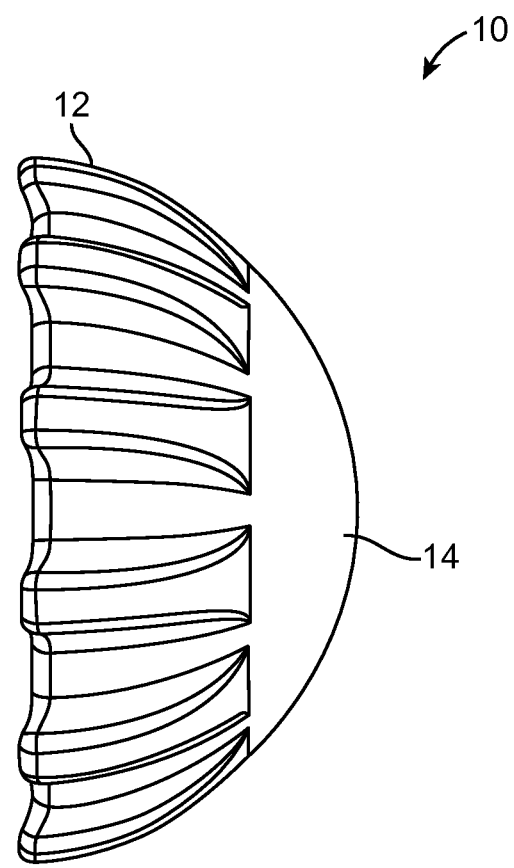
Figure 2F:
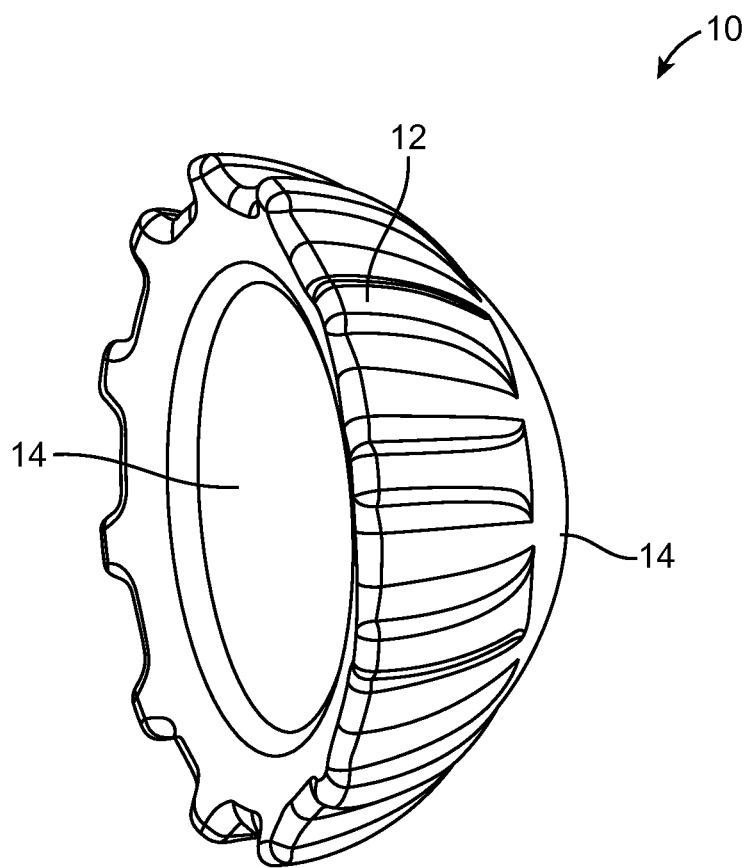
Figure 2G:
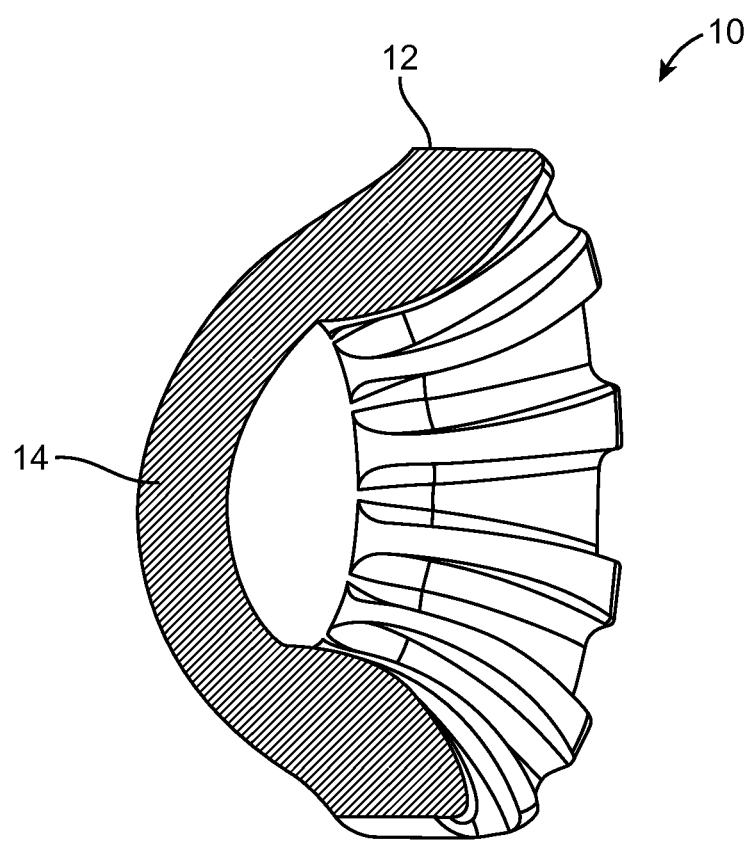
Figure 2H:
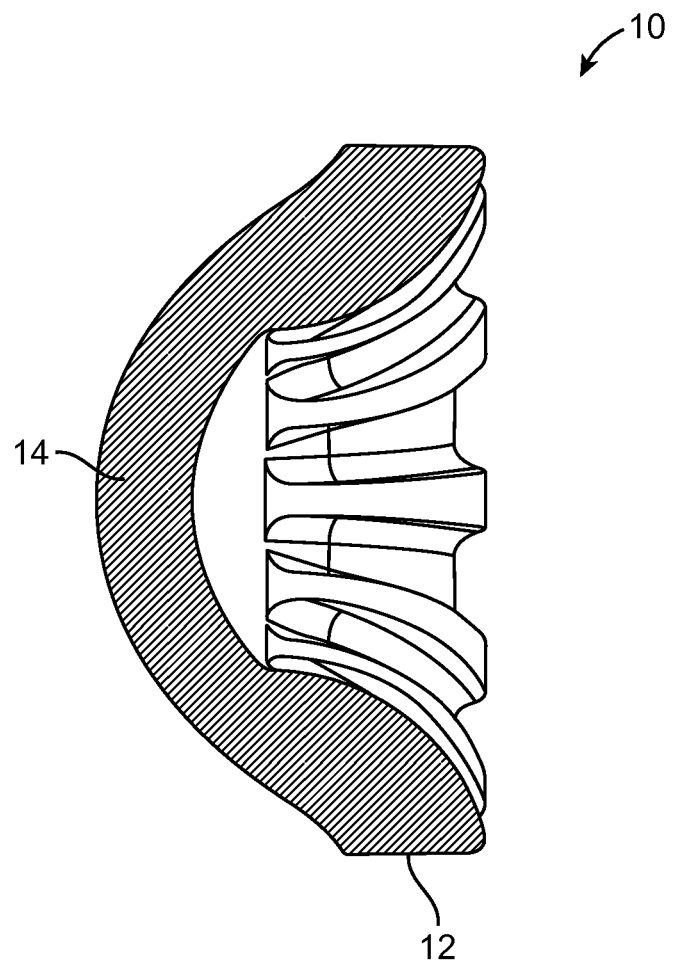
Figure 2I:
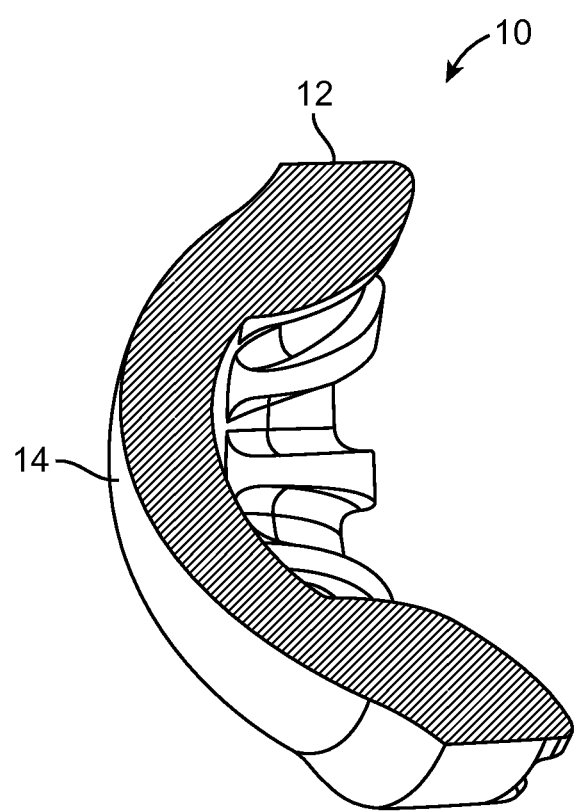
Figure 2J:
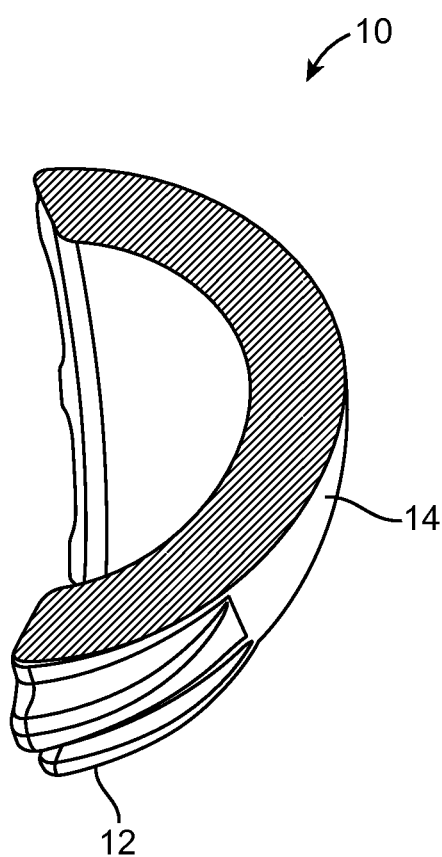
Figure 2K:
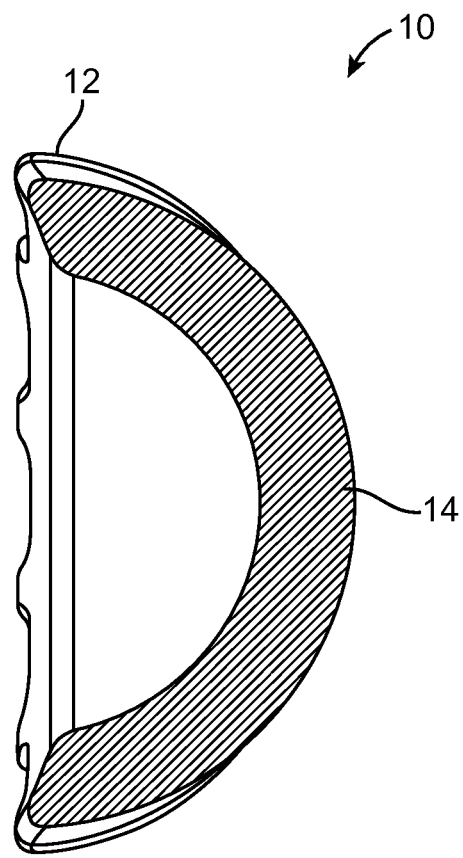
Figure 2L:
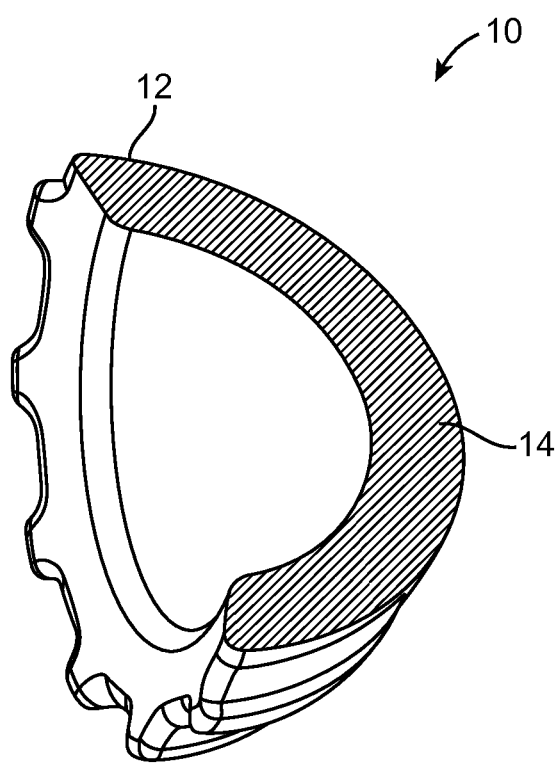

The drawings are not intended to be limiting, and various embodiments of the reconstitution devices described herein may be carried out in a variety of other ways, including ways not necessarily depicted in the drawings. Additionally, the drawings are not necessarily drawn to scale, and the disclosed embodiments are sometimes illustrated diagrammatically and in partial views. In certain instances, details which are not necessary for an understanding of the disclosed methods and apparatuses, or which render other details difficult to perceive, may have been omitted. This disclosure is not limited to the particular embodiments illustrated herein.

DETAILED DESCRIPTION

The following detailed description of various embodiments is not intended, and should not be interpreted, to limit the scope of the invention described by the claims. Any of a number of alternative features, aspects, configurations and the like may be incorporated into any of the embodiments described herein, without departing from the scope of the invention. Therefore, the following description of embodiments should be used for exemplary purposes only.

Reconstitution Devices

FIG. 1 shows various views of several different embodiments of reconstitution devices 10, 20, 30, 40, which are generally plunger devices (or "barriers") for insertion into cartridges or syringes, and which are shown in subsequent figures in more detail and described in further detail below. Generally speaking, a reconstitution device 10, 20, 30, 40 may be placed within a cartridge or syringe to form a seal with the inner wall of the cartridge or syringe and thus form two separate compartments—one on either side of reconstitution device 10, 20, 30, 40. A different substance or component of a substance may reside in each of the two formed compartments, and reconstitution device 10, 20, 30, 40 will keep the two substances or components separated until which time a user of the device causes the substances to mix. A force may be applied to reconstitution device 10, 20, 30, 40 to reconstitute the substance by mixing the two, previously separate components in one of the compartments of the syringe. For example, in some embodiments, force may be applied by advancing a syringe stopper in one compartment toward reconstitution device 10, 20, 30, 40. In other embodiments, any of a number of forces may be applied. In some embodiments, the force may be axially aligned with a longitudinal axis of the syringe or cartridge, although this is not necessary in all embodiments. The force applied may cause a portion of reconstitution device 10, 20, 30, 40 to roll, flip, pop, move, displace, or the like, to enable fluid communication between the two separate compartments within the syringe or cartridge.

FIGS. 2A-2L are various views of one embodiment of a one-part reconstitution device 10, having a flipping mechanism. Reconstitution device 10 has a generally semi-spherical shape 14 that may be flipped inside and out—i.e., from a first configuration, in which reconstitution device 10 will form a seal with an inner wall of a cartridge or syringe, to a second configuration, in which reconstitution device 10 will allow fluid communication between the two compartments of the cartridge or syringe. In this embodiment, reconstitution device 10 includes an outer, contact portion 12 (for contacting the inner wall of a cartridge or syringe) and an inner, deflection portion (for changing shape), which includes multiple ridges 16 and channels 17.

In the embodiment of FIGS. 2A-2L (as in many embodiments described below), reconstitution device 10 is a one-part device. By "one-part" or "one part," it is meant that the various features of reconstitution device 10 are not separate pieces attached to one another but are all part of the same, one-part construction. In many embodiments, but not necessarily, this one-part construction may be made from one piece of material. Alternatively, multiple materials may be blended or otherwise used together to achieve a one-part construction. The material (or materials) used to form one-part reconstitution device 10 may be any suitable polymer, shape memory material or other material that is sufficiently flexible to change shape from a first configuration to a second configuration.

FIGS. 2A-2C and 2G-2I show reconstitution device 10 in a first configuration, for forming a seal with a cartridge or syringe wall to form two compartments in the cartridge or syringe. FIGS. 2D-2F and 2J-2L show reconstitution device 10 inverted, in a second configuration, for allowing fluid to pass from one compartment to the other. In this embodiment, contact portion 12 will contact the inner wall of the cartridge or syringe to form the seal in the first configuration. In the second configuration, ridges 16 will contact the inner wall of the cartridge or syringe, allowing fluid flow through channels 17. In the first configuration, reconstitution device 10, through contact portion 12, applies a first amount of force against the inner wall of the cartridge or syringe. This amount of force will generally be sufficient to help form the seal with the inner wall and to maintain the seal and the position of reconstitution device 10 within the cartridge or syringe so long as any amount of opposing forces, such as axially directed force along the cartridge or syringe length, is not great enough to break the seal and move reconstitution device 10. When flipped from the first to the second configuration, reconstitution device 10, through ridges 16, applies a second amount of force against the inner wall of the cartridge or syringe, which is generally less than the first amount of force. This second amount of force will generally be small enough to allow reconstitution device 10 to be smoothly advanced through the cartridge or syringe.

Figure 3D:
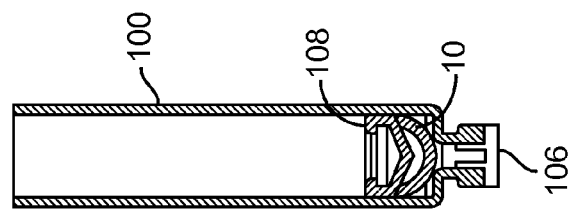
FIGS. 3A-3H are various views of a syringe and the reconstitution device of FIGS. 2A-2L, illustrating operation of the device, according to one embodiment.
Figure 3C:
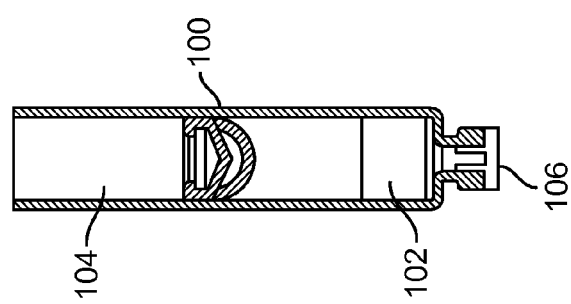
Figure 3B:
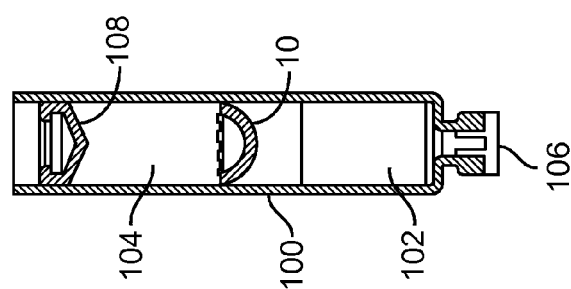
Figure 3A:
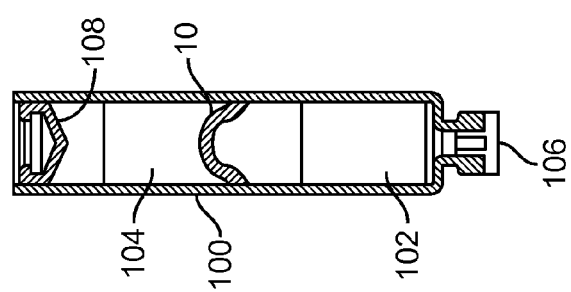
Figure 3H:
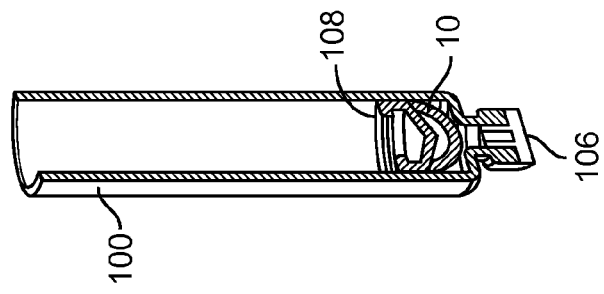
Figure 3G:
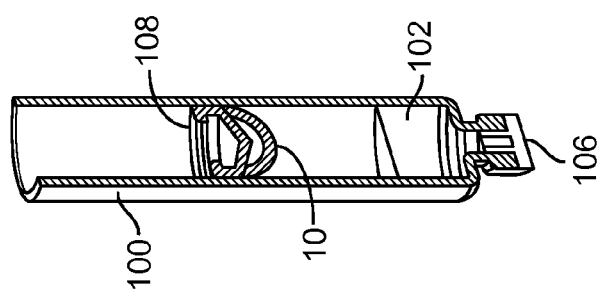
Figure 3F:
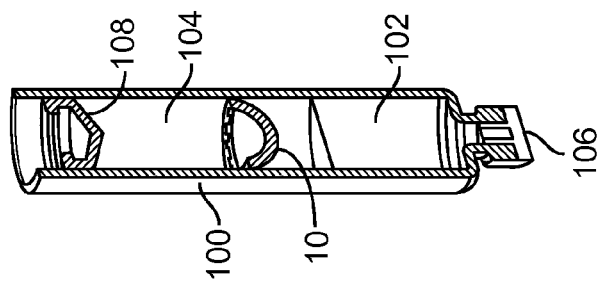
Figure 3E:
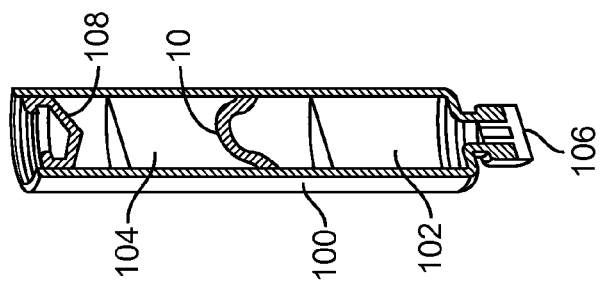
Figure 4A:
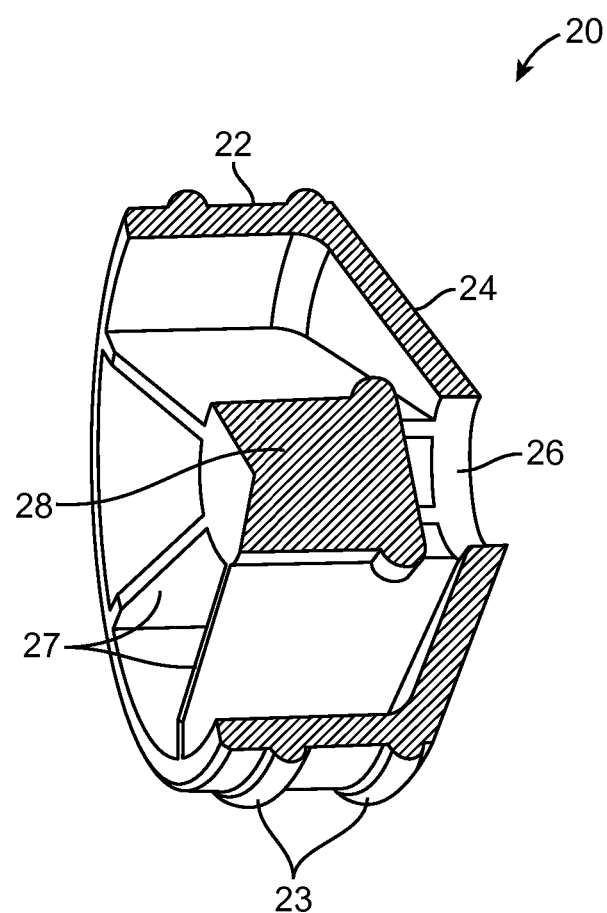
FIGS. 4A-4J are various views of a one-part reconstitution device having a peg that in a first position blocks fluid flow through the center of the device, according to an alternative embodiment.
Figure 4B:
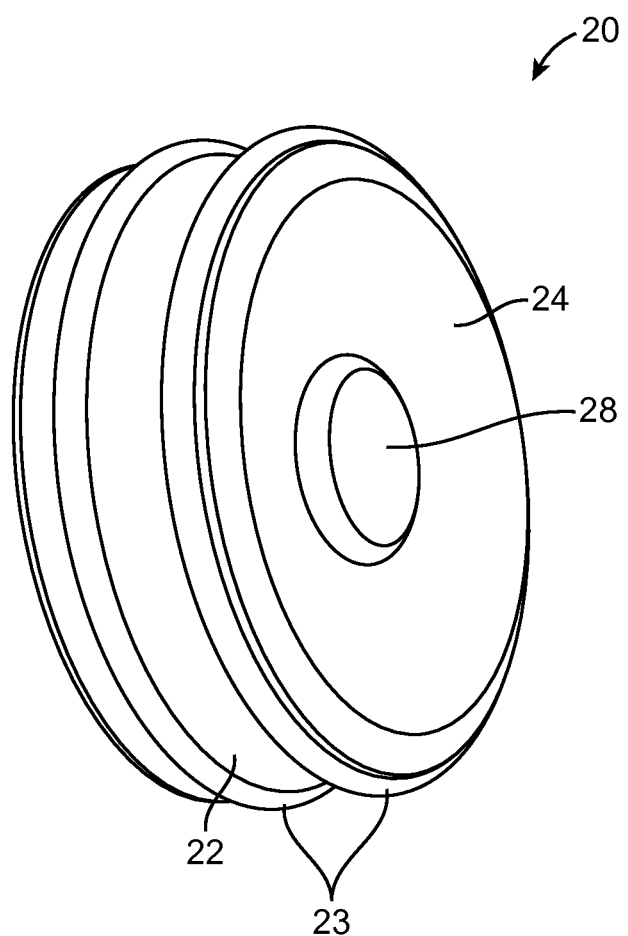
Figure 4C:
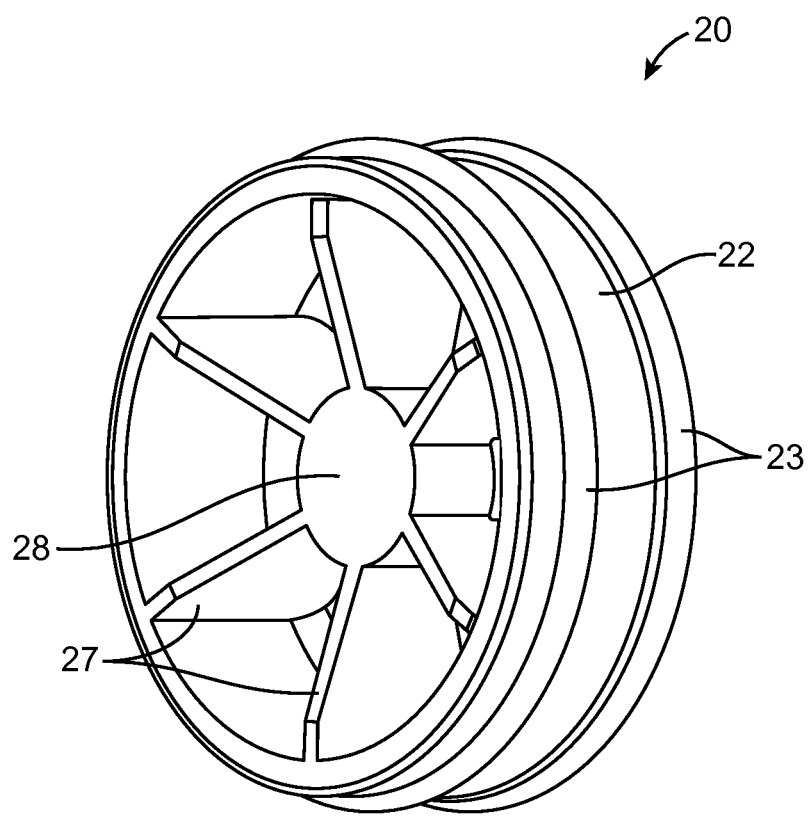
Figure 4D:
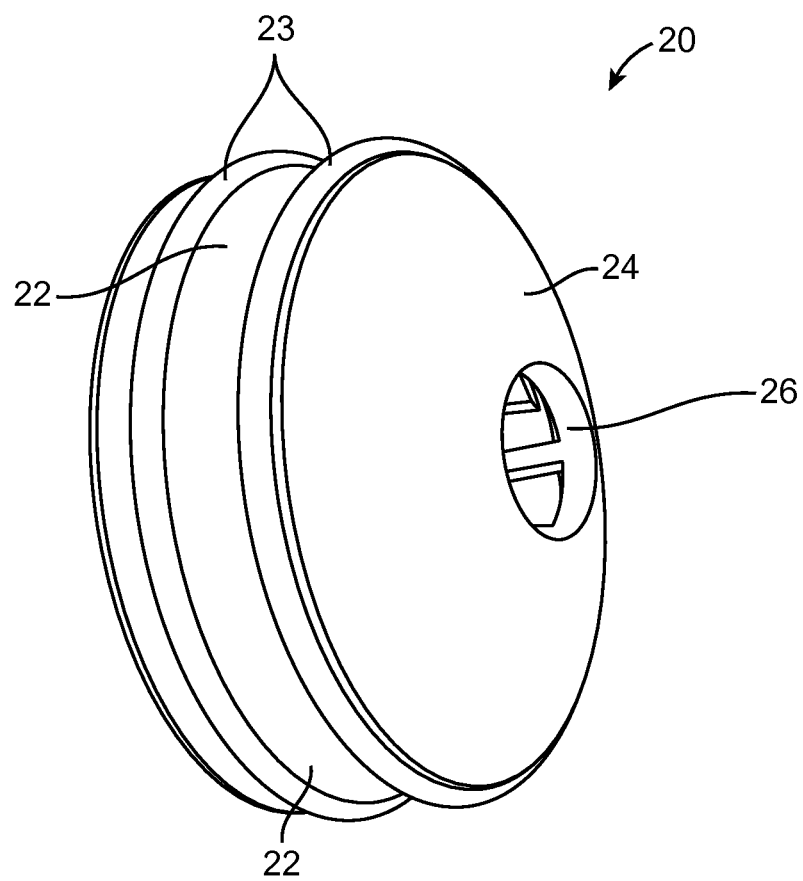
Figure 4E:
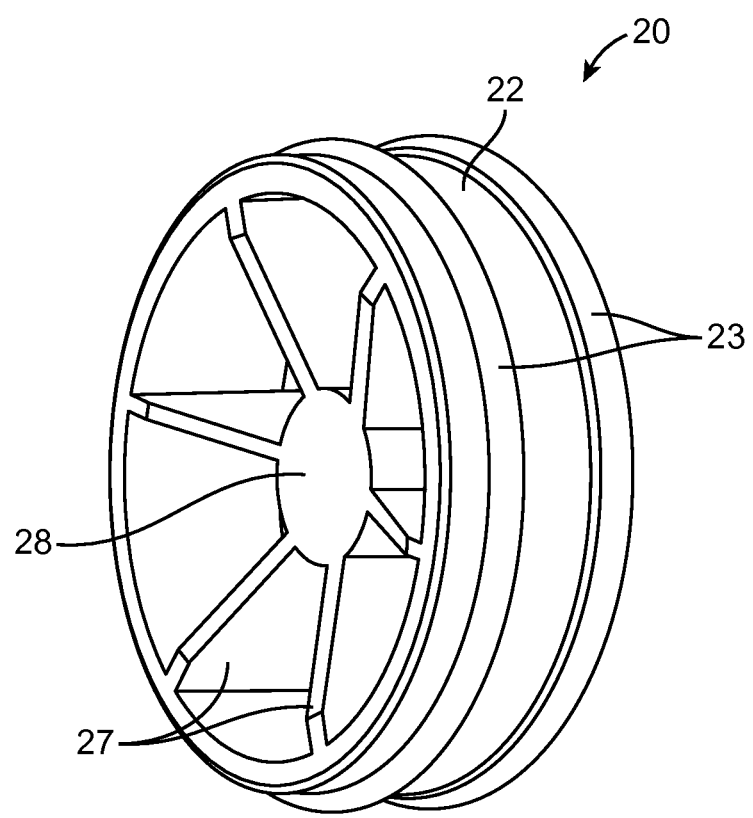
Figure 4F:
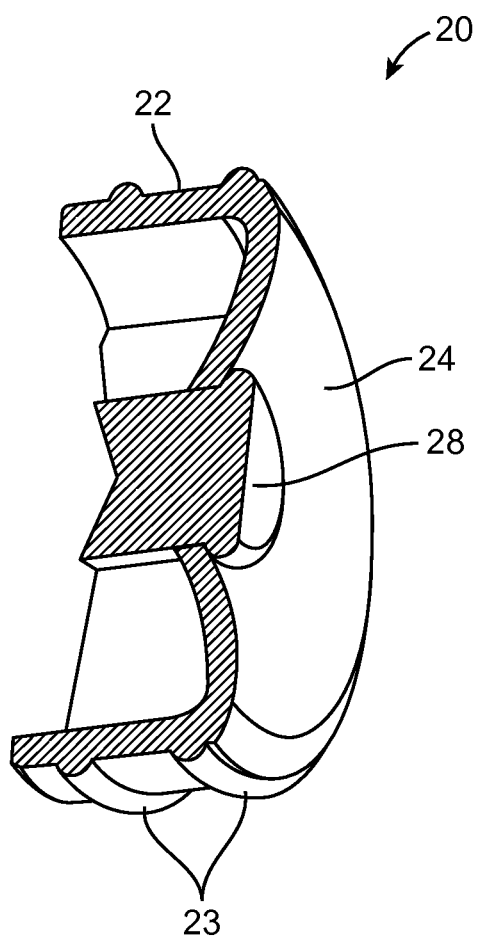
Figure 4G:
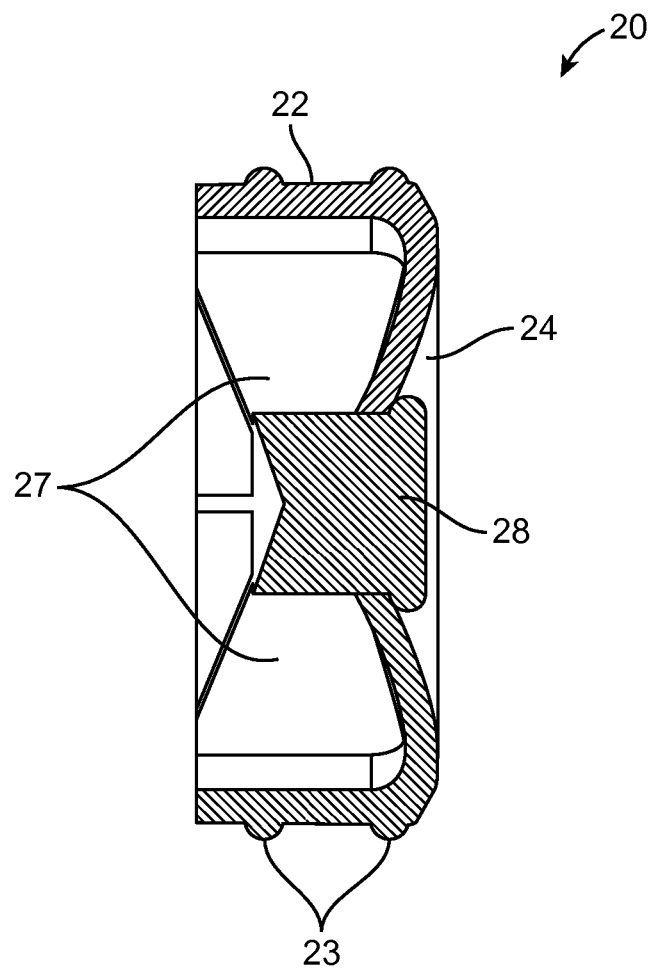
Figure 4H:
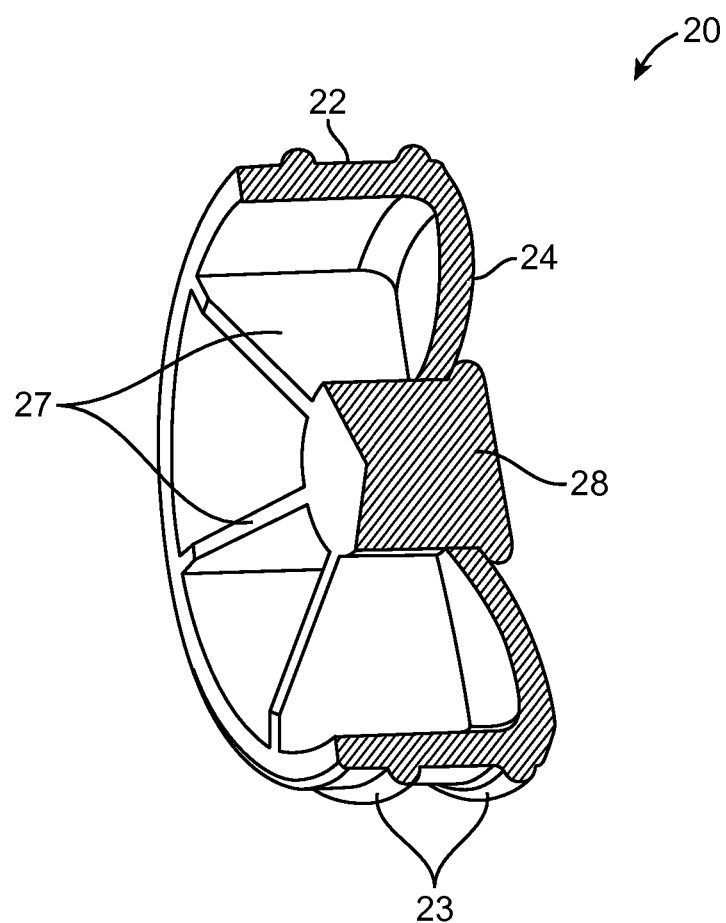
Figure 4I:
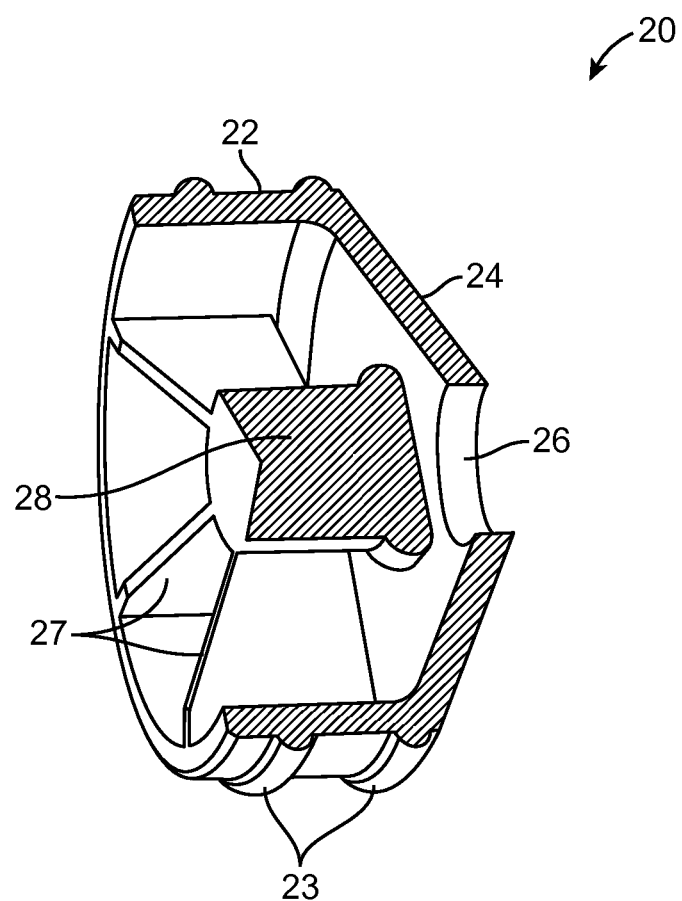
Figure 4J:
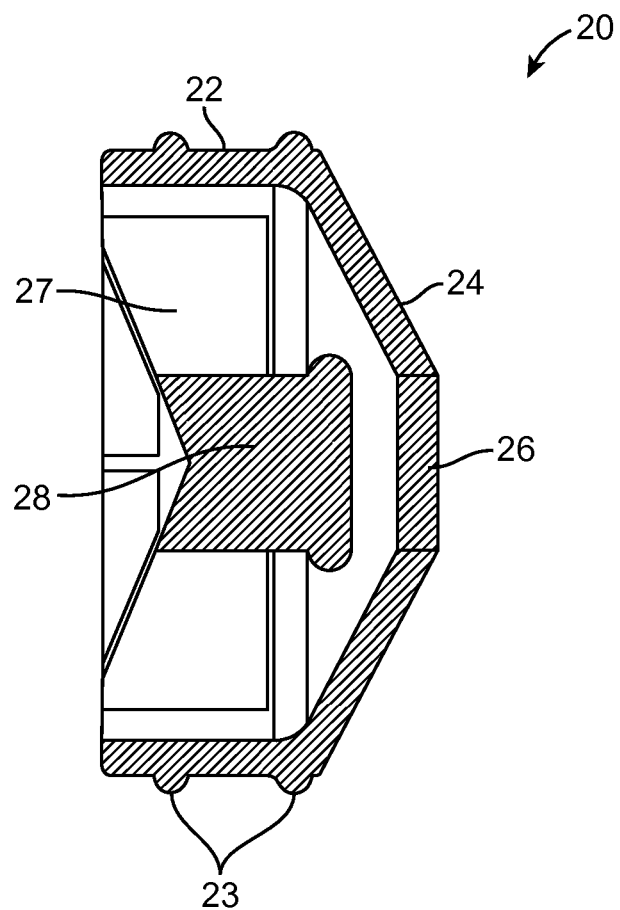

FIGS. 3A-3H illustrate use of reconstitution device 10 in a syringe 100. FIGS. 3E-3H are simply perspective views of the same steps shown in FIGS. 3A-3D, so the two sets of figures will only be described once, in reference to FIGS. 3A-3D. In FIG. 3A, reconstitution device 10 is disposed in syringe 100 in its first configuration, forming a seal with the inner wall of syringe 100, and thus forming two, separate compartments 102, 104 on either side of reconstitution device 10. Compartments 102, 104 may have any suitable form of substance located therein—i.e., fluid(s), solid(s) and/or gas(es)—according to various embodiments. Syringe 100 also includes a stopper 108 at one end and a medication exit port at an opposite end 106, where a needle might be attached. Reconstituted medication or other fluid generally exits through end 106, after reconstitution.

Referring to FIG. 3B, when stopper 108 is advanced through syringe 100, toward reconstitution device 10, the force generated in compartment 104 against reconstitution device 10 causes it to flip into its second configuration, thus allowing the flow of fluid from compartment 104 to compartment 102. This force is generated, in this embodiment, by pushing against fluid (typically liquid with or without air) with stopper 108, thus compressing the fluid and generating pressure. As shown in FIG. 3C, the stopper 108 may be advanced farther through syringe 100 to meet with reconstitution device 10. Finally, as illustrated in FIG. 3D, stopper 108 may be further advanced, along with reconstitution device 10, such that stopper 108 and reconstitution device 10 essentially act together as a plunger, causing the reconstituted medication to exit syringe 100 out of end 106. This is only one embodiment of a method for using reconstitution device 10. For example, in another embodiment, reconstitution device 10 may be used in a cartridge rather than syringe 100. In various embodiments, syringe 100 may be of any suitable size, and thus multiple different sizes of reconstitution device 10 may be provided, for use in the different variations of syringe 100. Furthermore, as suggested above, this or any alternative embodiment may be used to mix or reconstitute any substances or combinations of substances. Thus, no embodiments herein are limited to one particular use, medication, syringe, cartridge or the like.

FIGS. 4A-4J are various views of an alternative embodiment of a one-part reconstitution device 20. In this embodiment, reconstitution device 20 includes an outer, contact portion 22, including two circumferential ribs 23, an inner, deflection portion 24 (or "disc"), coupled with one end of contact portion 22 and including a hole 26, and a plug 28 (or "peg") coupled with the contact portion 22 and the deflection portion 24 via multiple connectors 27. Similar to the previously described embodiment, reconstitution device 20 is a one-part device. In use, deflection portion 24 moves between a first configuration, in which plug 28 blocks hole 26 and thus maintains the sealed separation between two compartments of a cartridge or syringe, and a second configuration, in which deflection portion 24 is dislodged and moved away from plug 28 to open up hole 26 and allow fluid to flow through reconstitution device 20 for reconstitution of the substance.

FIGS. 4B, 4C and 4F-4H show reconstitution device 20 in the first, locked configuration, with peg 28 lodged in hole 26. FIGS. 4A, 4D, 4E, 4I and 4J show reconstitution device 20 with peg 28 dislodged from hole 26 and disc 24 urged away from peg 28. Ribs 23 may help reconstitution device 20 form a seal with an inner wall of a cartridge or syringe. As mentioned previously, reconstitution device 20 may be made of any suitable material.

Figure 5D:
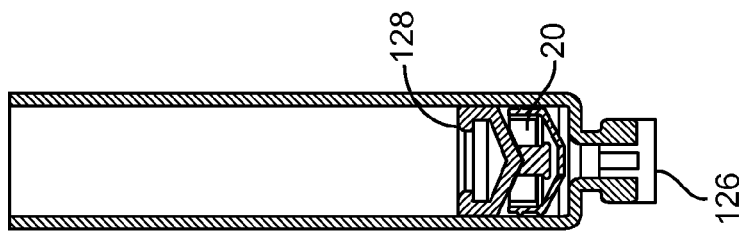
FIGS. 5A-5H are various views of a syringe and the reconstitution device of FIGS. 4A-4J, illustrating operation of the device, according to one embodiment.
Figure 5C:
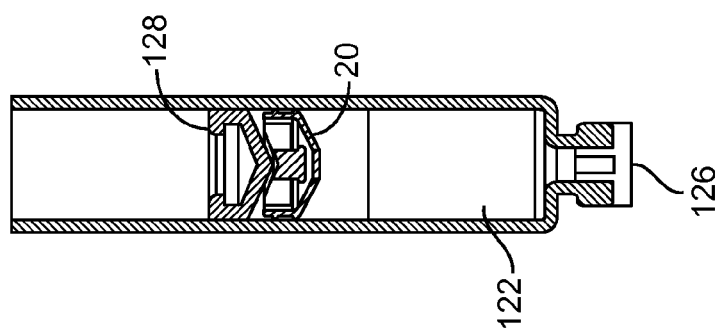
Figure 5B:
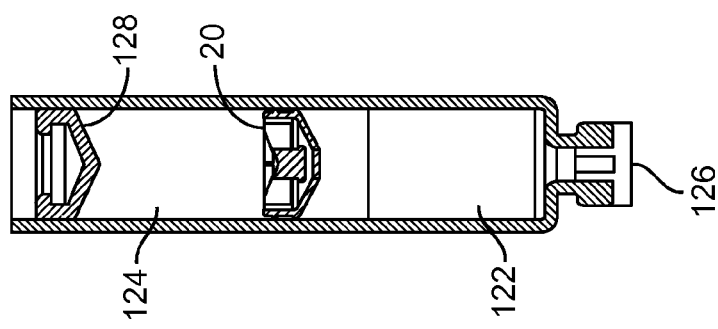
Figure 5A:
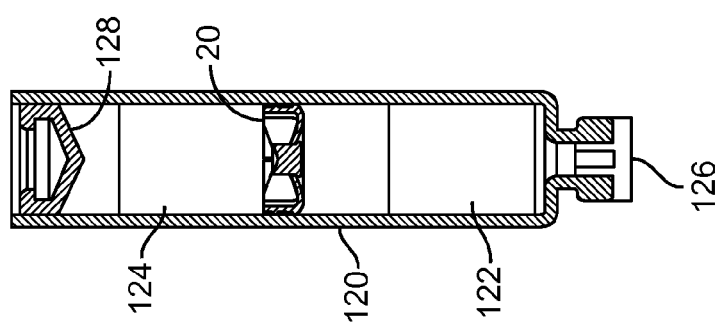
Figure 5H:
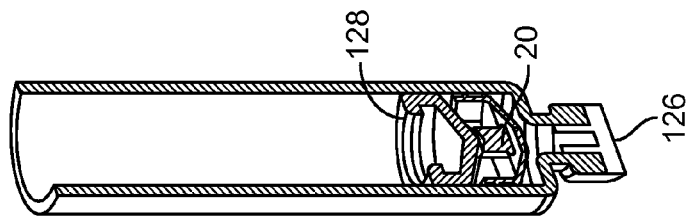
Figure 5G:
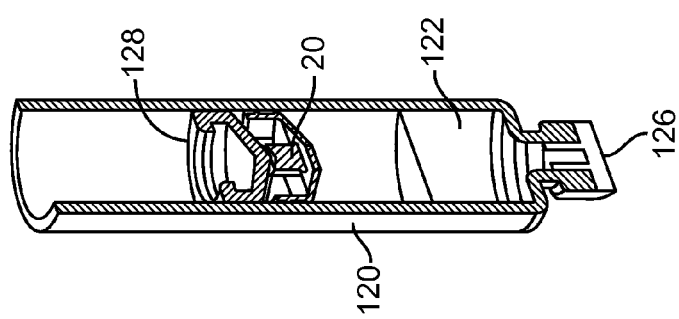
Figure 5F:
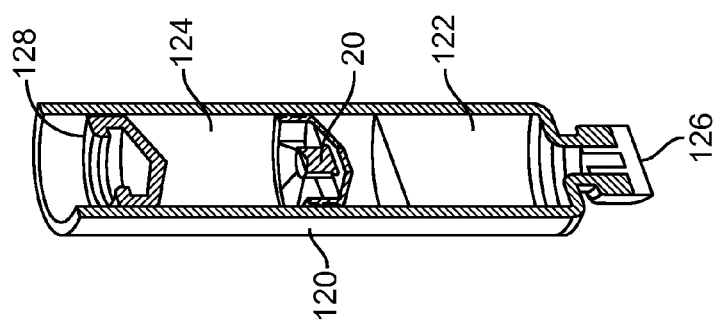
Figure 5E:
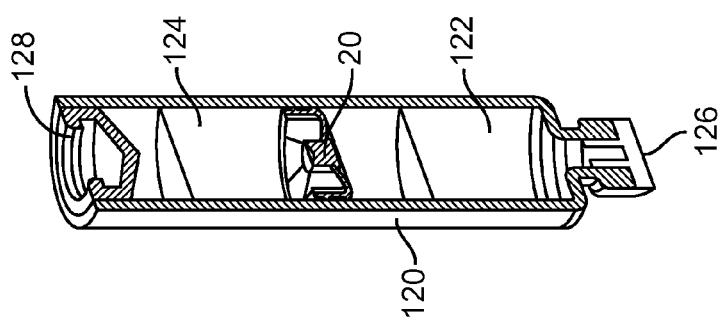

FIGS. 5A-5H illustrate use of reconstitution device 20 in a syringe 120. FIGS. 5E-5H are simply perspective views of the same steps shown in FIGS. 5A-5D, so the two sets of figures will only be described once, in reference to FIGS. 5A-5D. In FIG. 5A, reconstitution device 20 is disposed in syringe 120 in its first configuration, with plug 28 in hole 26, forming a seal with the inner wall of syringe 120, and thus forming two, separate compartments 122, 124 on either side of reconstitution device 20. Compartments 122, 124 may have any suitable form of substance located therein—i.e., fluid(s), solid(s) and/ or gas(es)—according to various embodiments. Syringe 120 also includes a stopper 128 at one end and a medication exit port at an opposite end 126, where a needle might be attached. Reconstituted medication or other fluid generally exits through end 126, after reconstitution.

Referring to FIG. 5B, when stopper 128 is advanced through syringe 120, toward reconstitution device 20, the force generated in compartment 124 against reconstitution device 20 causes deflection portion 24 to deflect and thus disengage hole 26 from plug 28, allowing the flow of fluid from compartment 124 to compartment 122. This force is generated, in this embodiment, by pushing against fluid (typically liquid with or without air) with stopper 128, thus compressing the fluid and generating pressure. As shown in FIG. 5C, the stopper 128 may be advanced farther through syringe 120 to meet with reconstitution device 20. Finally, as illustrated in FIG. 5D, stopper 128 may be further advanced, along with reconstitution device 20, such that stopper 128 and reconstitution device 20 essentially act together as a plunger, causing the reconstituted medication to exit syringe 120 out of end 126. This is only one embodiment of a method for using reconstitution device 20. For example, in another embodiment, reconstitution device 20 may be used in a cartridge rather than syringe 120. In various embodiments, syringe 120 may be of any suitable size, and thus multiple different sizes of reconstitution device 20 may be provided, for use in the different variations of syringe 120. Furthermore, as suggested above, this or any alternative embodiment may be used to mix or reconstitute any substances or combinations of substances. Thus, no embodiments herein are limited to one particular use, medication, syringe, cartridge or the like.

FIGS. 6A-6G are various views of an alternative embodiment of a one-part reconstitution device 30. In this embodiment, reconstitution device 30 includes an outer, contact portion 32, including multiple, circumferential ribs 33, a central opening 36, an inner, deflection portion 34, including multiple apertures 35 (or "perforations"), and a peg 38 (or "plug") coupled with the deflection portion 34. Deflection portion 34, in communication with peg 38, rolls forward to enable peg 38 to dislodge. Apertures 35 allow for fluid communication through reconstitution device 30. Similar to the previously described embodiments, reconstitution device 30 is a one-part device. In use, deflection portion 34 moves between a first configuration, in which peg 38 and deflection portion 34 block central opening 36 and thus maintain the sealed separation between two compartments of a cartridge or syringe, and a second configuration, in which deflection portion 34 flips open to a straighter form, thus moving peg 38 into central opening 36 and allowing fluid to flow through apertures 35 for reconstitution of the substance.

Figure 6A:
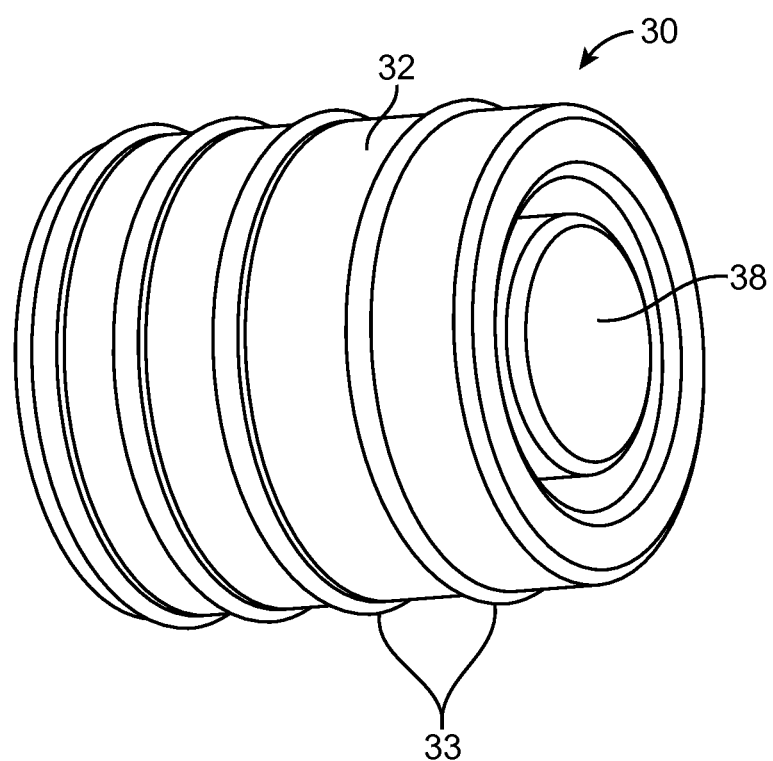
FIGS. 6A-6G are various views of a one-part reconstitution device having a valve mechanism, according to another alternative embodiment.
Figure 6B:
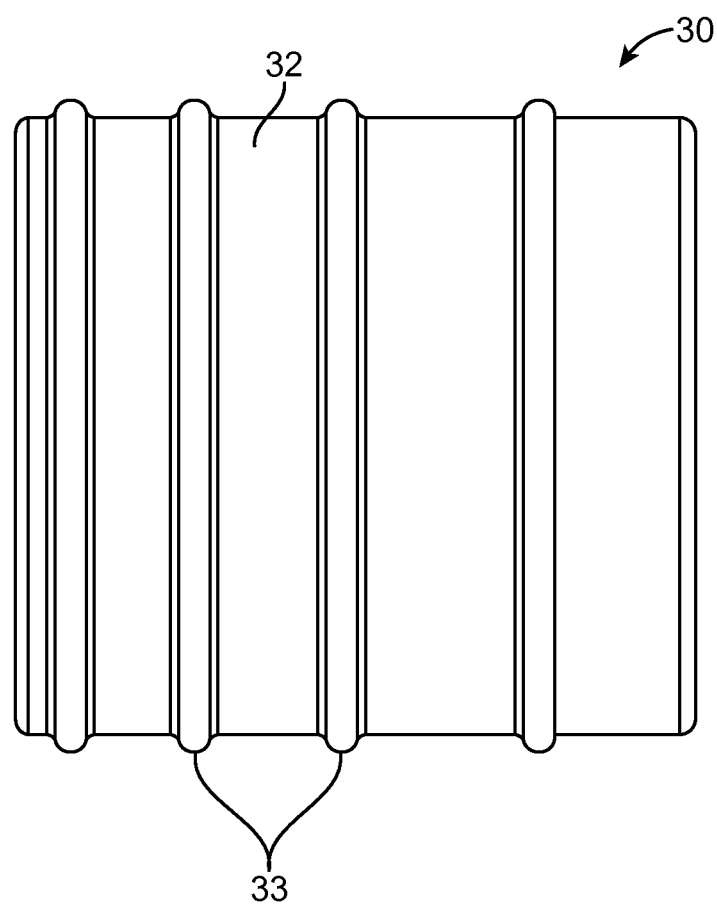
Figure 6C:
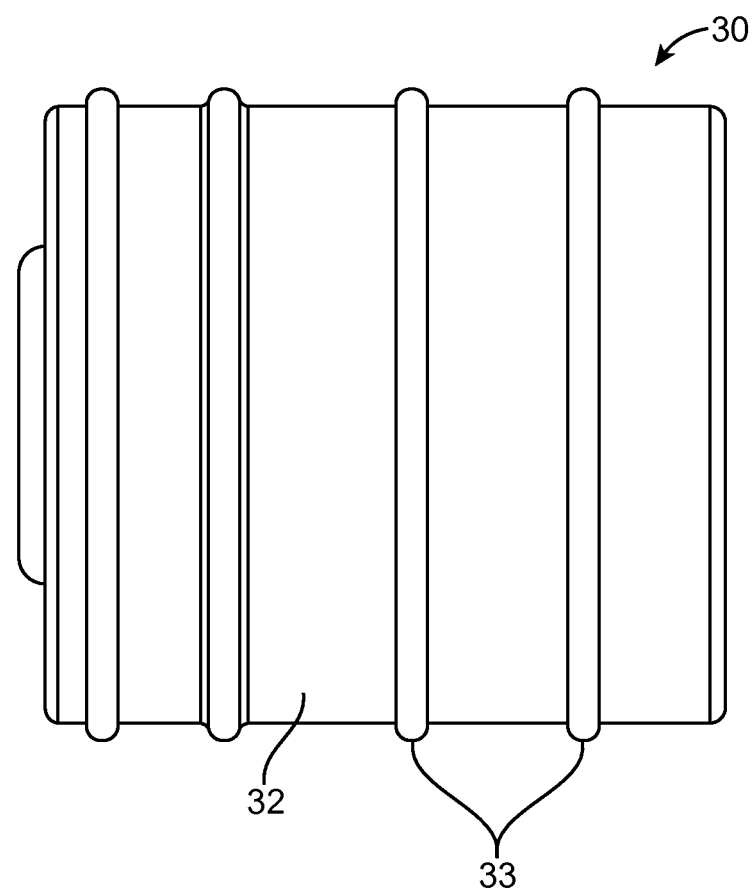
Figure 6D:
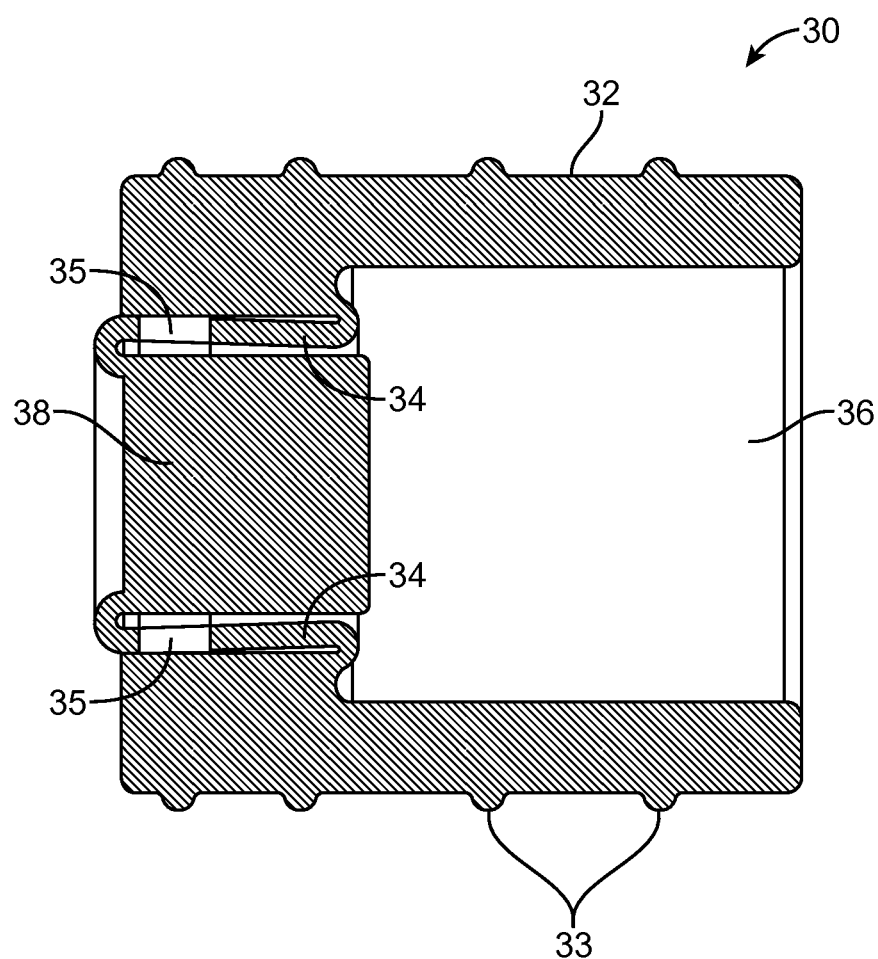
Figure 6E:
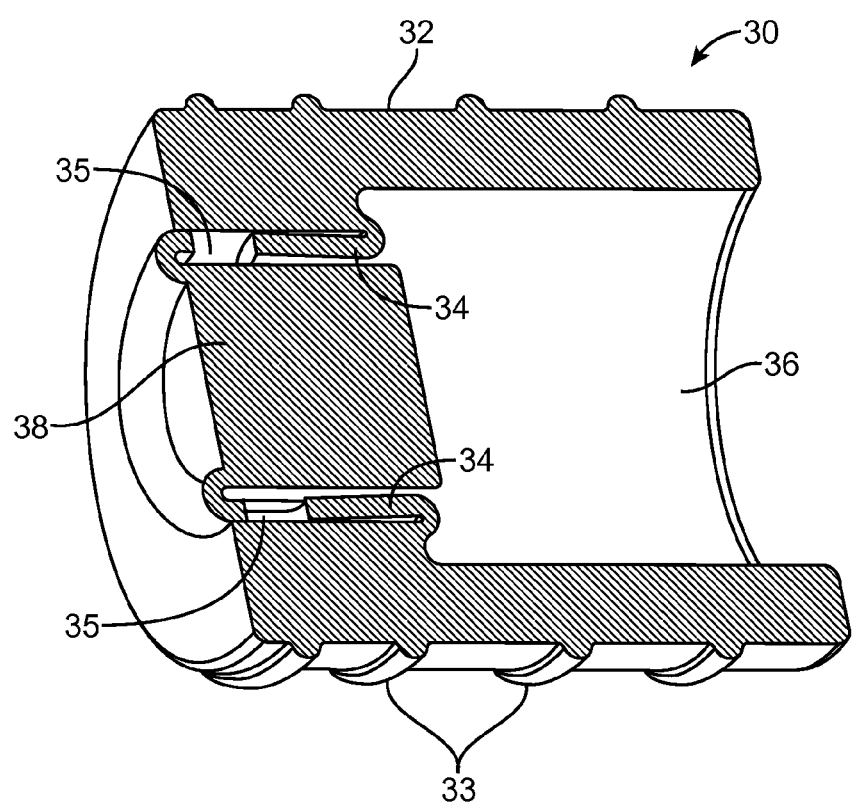
Figure 6F:
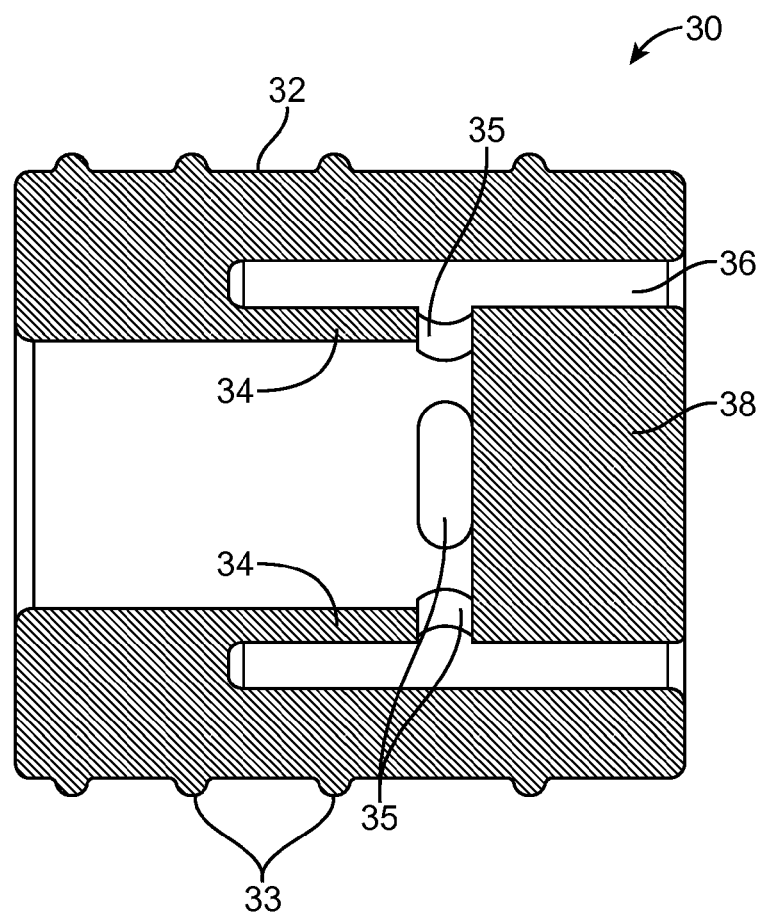
Figure 6G:
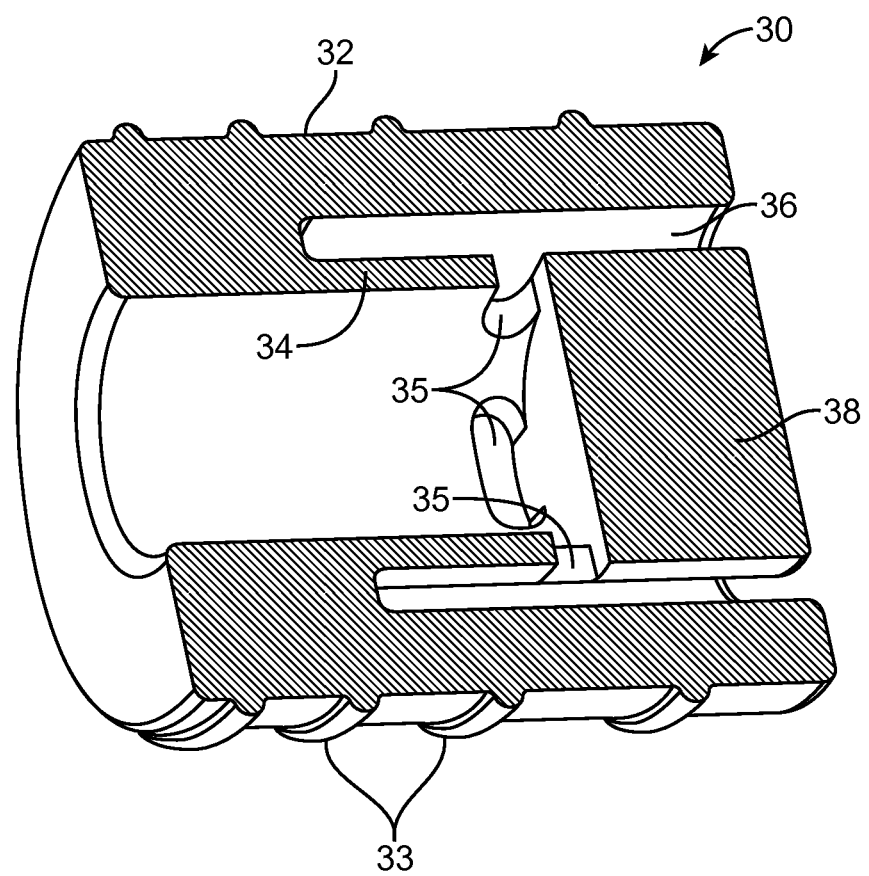

FIGS. 6A and 6C-6E show reconstitution device 30 in the first, locked configuration, with peg 38 and deflection portion 34 blocking fluid flow. FIGS. 6B, 6F and 6G show reconstitution device 30 with peg 38 and deflection portion 34 dislodged from the locked position and apertures 35 open to allow fluid flow. Ribs 33 may help reconstitution device 30 form a seal with an inner wall of a cartridge or syringe. As mentioned previously, reconstitution device 30 may be made of any suitable material.

Figure 7D:
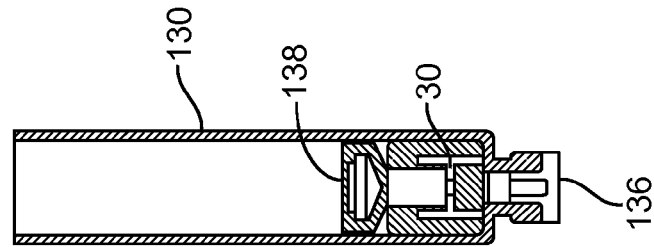
FIGS. 7A-7H are various views of a syringe and the reconstitution device of FIGS. 6A-6G, illustrating operation of the device, according to one embodiment.
Figure 7C:
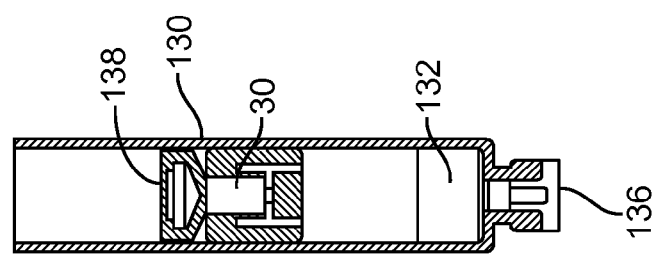
Figure 7B:
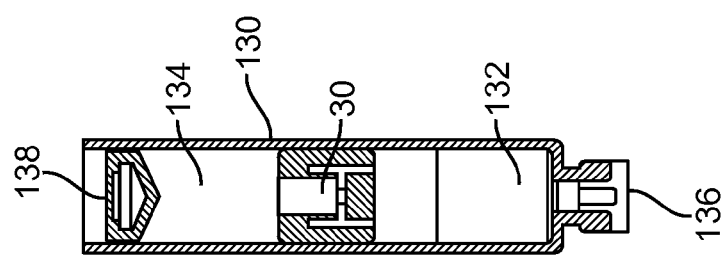
Figure 7A:
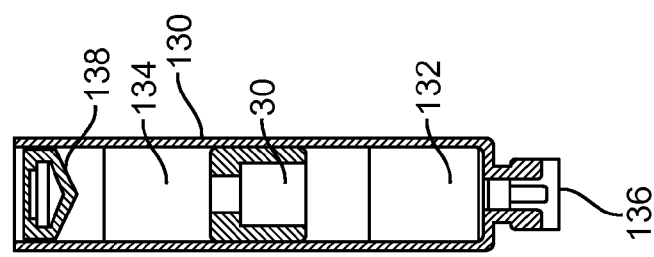
Figure 7H:
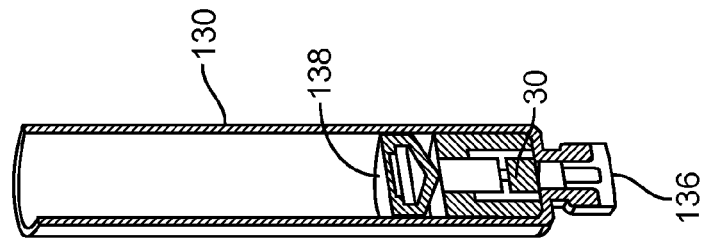
Figure 7G:
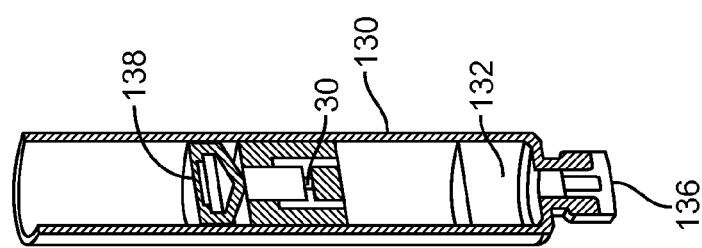
Figure 7F:
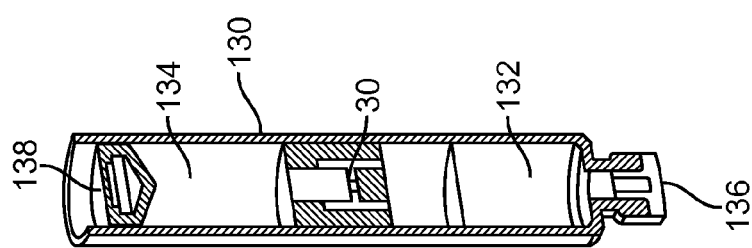
Figure 7E:
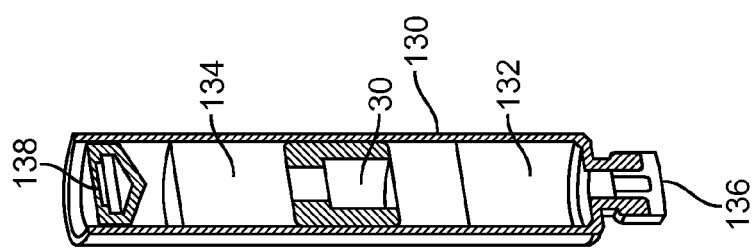
Figure 8A:
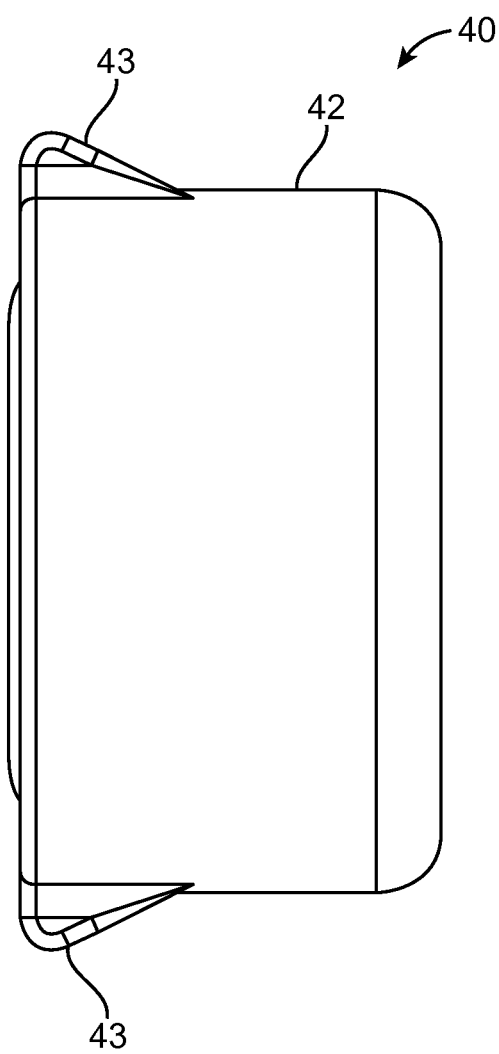
FIGS. 8A-8J are various views of a one-part reconstitution device having a flipping mechanism of action, according to another alternative embodiment.
Figure 8B:
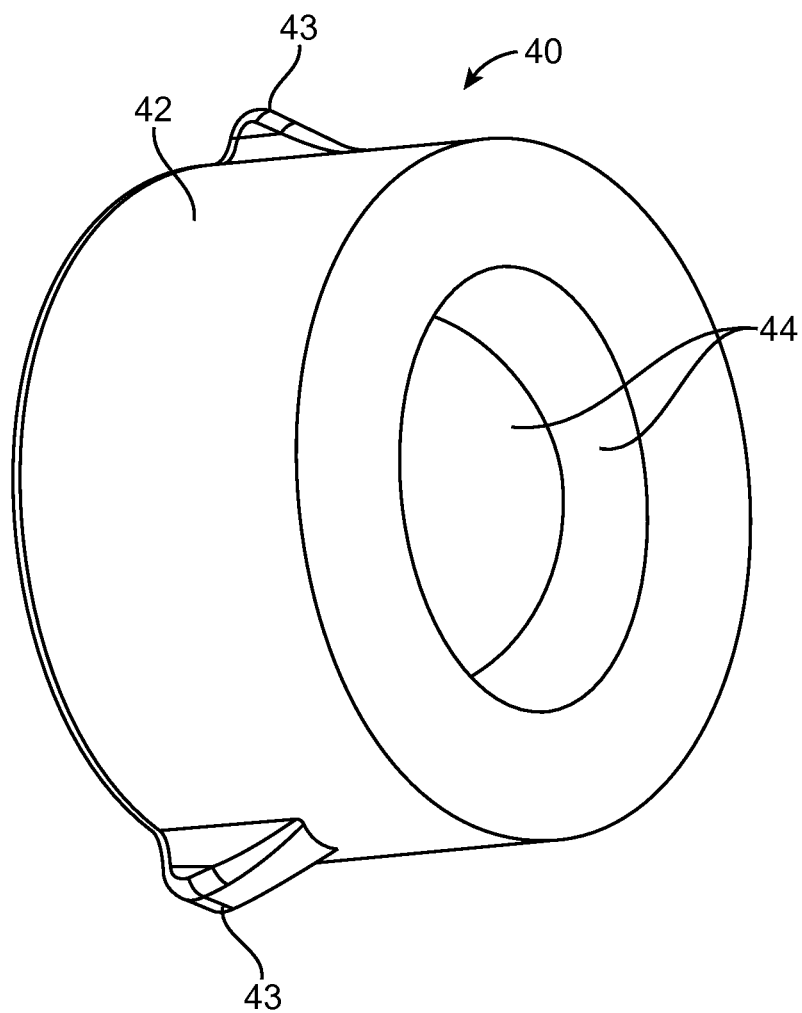
Figure 8C:
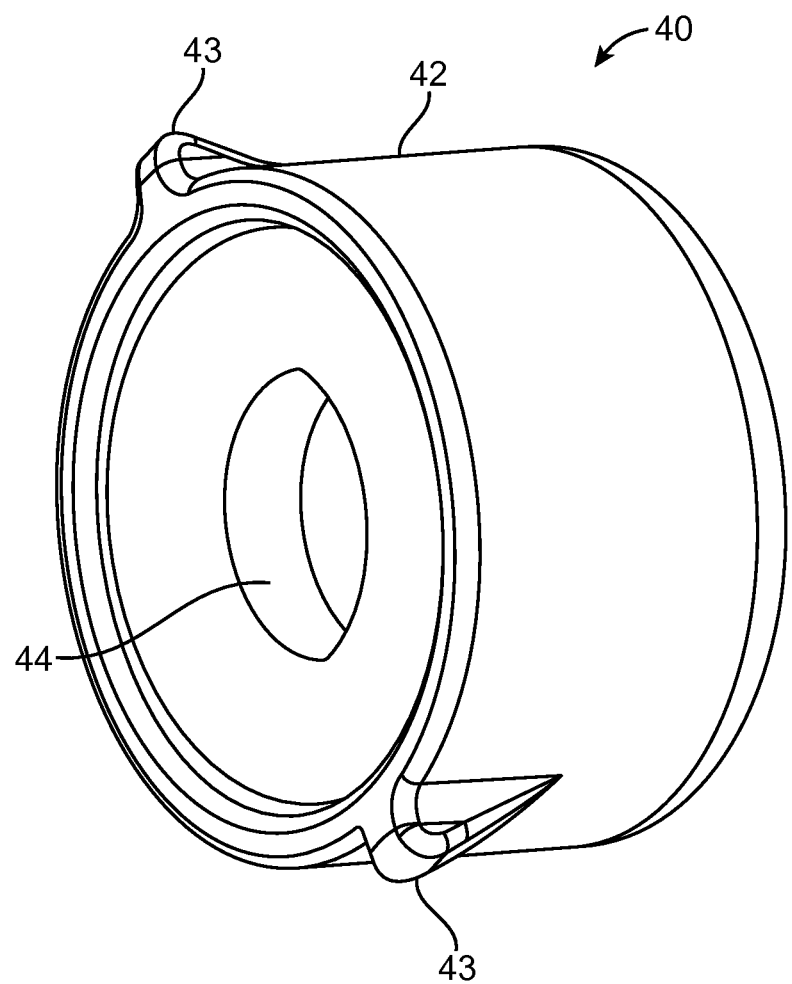
Figure 8D:
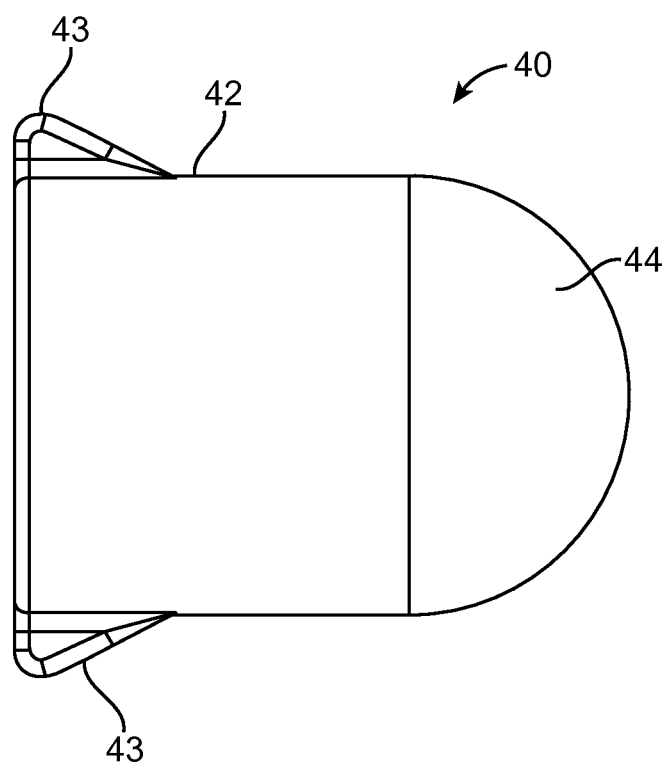
Figure 8E:
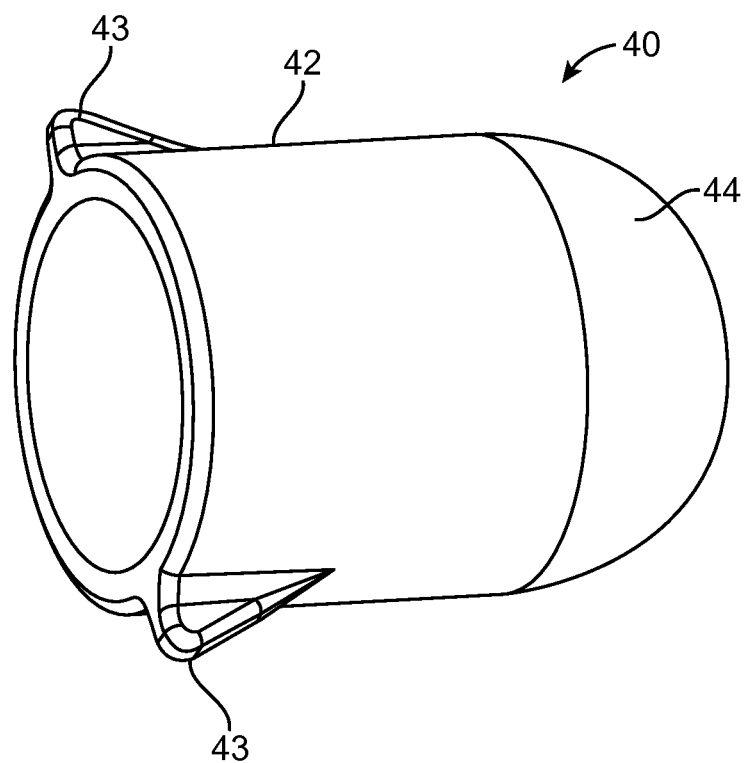
Figure 8F:
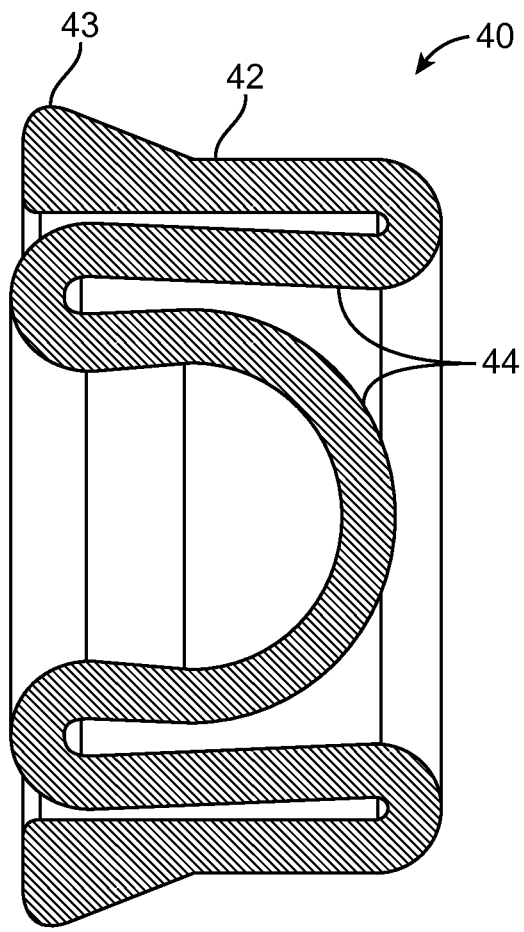
Figure 8G:
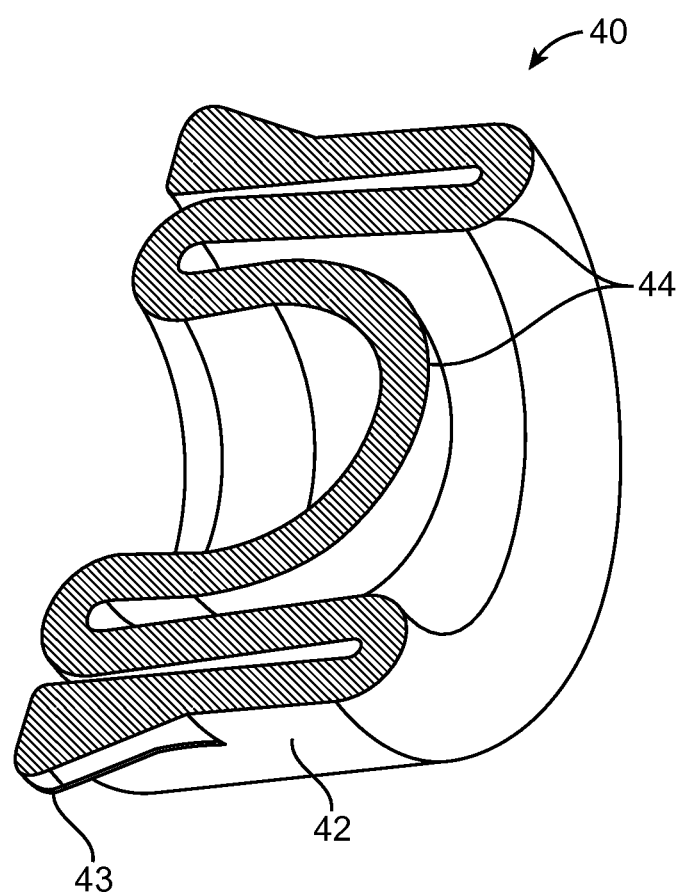
Figure 8H:
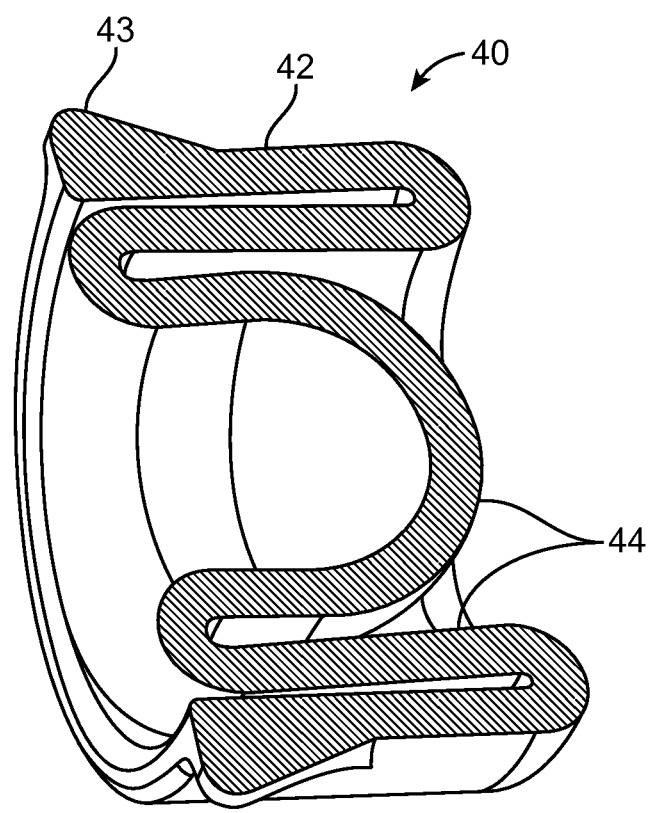
Figure 8I:
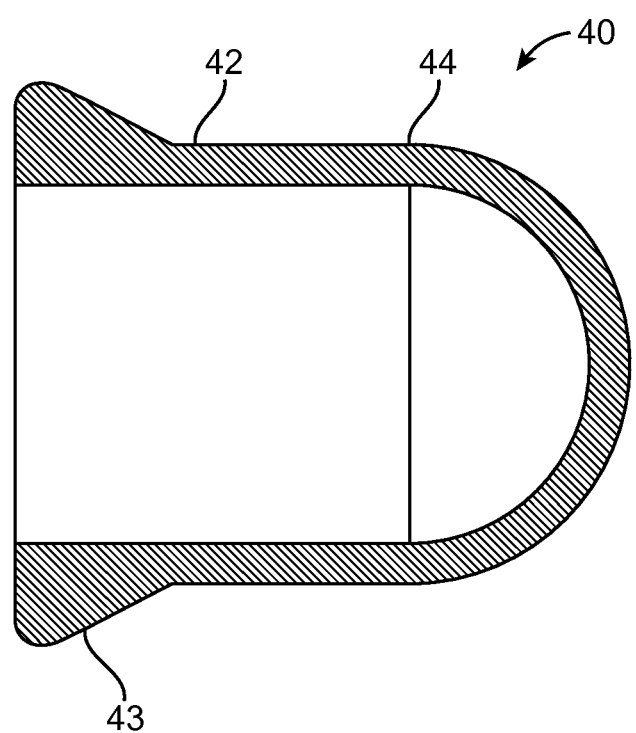
Figure 8J:
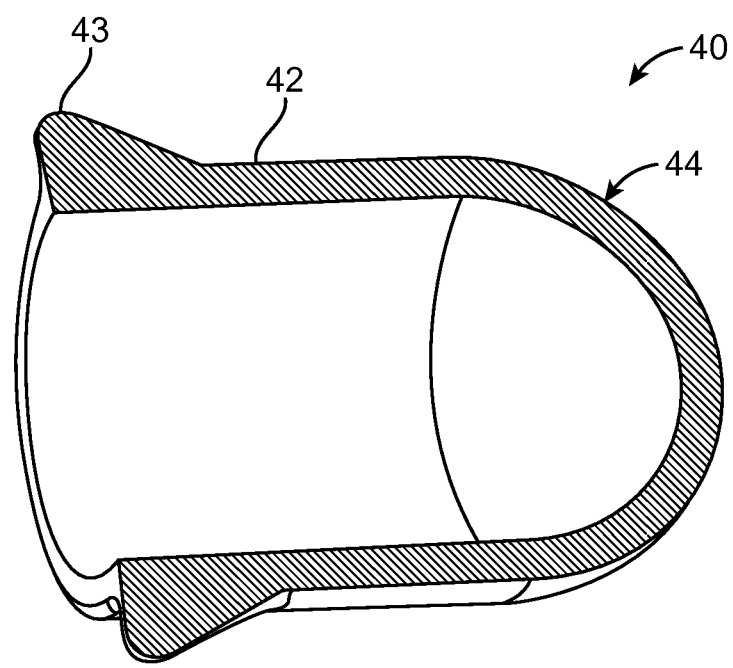

FIGS. 7A-7H illustrate use of reconstitution device 30 in a syringe 130. FIGS. 7E-7H are simply perspective views of the same steps shown in FIGS. 7A-7D, so the two sets of figures will only be described once, in reference to FIGS. 7A-7D. In FIG. 7A, reconstitution device 30 is disposed in syringe 130 in its first configuration, with peg 38 and deflection portion 34 lodged in the locked position, and with a seal formed with the inner wall of syringe 130, thus forming two, separate compartments 132, 134 on either side of reconstitution device 30. Compartments 132, 134 may have any suitable form of substance located therein—i.e., fluid(s), solid(s) and/or gas (es)—according to various embodiments. Syringe 130 also includes a stopper 138 at one end and a medication exit port at an opposite end 136, where a needle might be attached. Reconstituted medication or other fluid generally exits through end 136, after reconstitution.

Referring to FIG. 7B, when stopper 138 is advanced through syringe 130, toward reconstitution device 30, the force generated in compartment 134 against reconstitution device 30 causes deflection portion 34 to deflect and thus dislodge peg 38 and deflection portion 34, thus opening apertures 35. As stopper 138 advances, peg 38 advances in the direction that stopper 138 moves and deflection portion 134 rolls toward peg 38, such that apertures 35 open to establish fluid communication through reconstitution device 30. This configuration allows fluid to flow from compartment 134 to compartment 132, through apertures 35 and central opening 36. The force is generated, in this embodiment, by pushing against fluid (typically liquid with or without air) with stopper 138, thus compressing the fluid and generating pressure. As shown in FIG. 7C, the stopper 138 may be advanced farther through syringe 130 to meet with reconstitution device 30. Finally, as illustrated in FIG. 7D, stopper 138 may be further advanced, along with reconstitution device 30, such that stopper 138 and reconstitution device 30 essentially act together as a plunger, causing the reconstituted medication to exit syringe 130 out of end 136. This is only one embodiment of a method for using reconstitution device 30. For example, in another embodiment, reconstitution device 30 may be used in a cartridge rather than syringe 130. In various embodiments, syringe 130 may be of any suitable size, and thus multiple different sizes of reconstitution device 30 may be provided, for use in the different variations of syringe 130. Furthermore, as suggested above, this or any alternative embodiment may be used to mix or reconstitute any substances or combinations of substances. Thus, no embodiments herein are limited to one particular use, medication, syringe, cartridge or the like.

FIGS. 8A-8J are various views of an alternative embodiment of a one-part reconstitution device 40. In this embodiment, reconstitution device 40 includes an outer, contact portion 42 with surface features 43, and an inner, deflection portion 44 with a semi-spherical cap that lodges in reconstitution device 40. FIGS. 8A-8C and 8F-8H show reconstitution device 40 in a first, locked configuration, with the deflection portion/cap 44 retracted within reconstitution device 40. Deflection portion 44 rolls over on itself twice, but may roll fewer or more times in alternative embodiments. In the first configuration, reconstitution device 40 will push outwardly against an inner wall of a cartridge or syringe with a first amount of force to form a seal with the inner wall, prevent slippage of reconstitution device 40 along the inner wall, and thus plug the fluid path in the cartridge or syringe and keep two substances separated therein. Surface features 43 may help reconstitution device 40 form a seal with an inner wall of a cartridge or syringe. As mentioned previously, reconstitution device 40 may be made of any suitable material.

FIGS. 8C-8E, 8I and 8J show reconstitution device 40 in a second, unlocked configuration, with the cap advanced and deflection portion 44 rolled towards the cap to allow the cap to advance. In the second configuration, reconstitution device (40) pushes outward with a second amount of force, which is less than the first amount of force, so that fluid communication is allowed around reconstitution device 40.

Figure 9D:
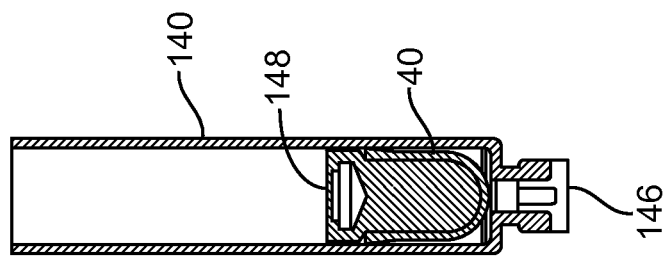
FIGS. 9A-9H are various views of a syringe and the reconstitution device of FIGS. 8A-8J, illustrating operation of the device, according to one embodiment.
Figure 9C:
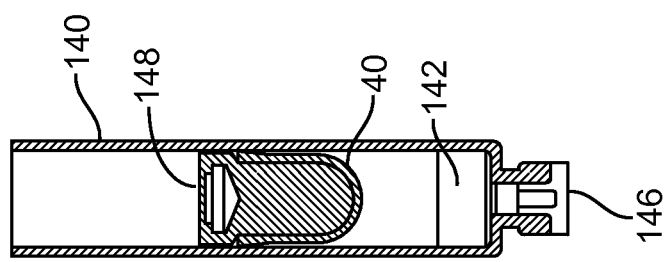
Figure 9B:
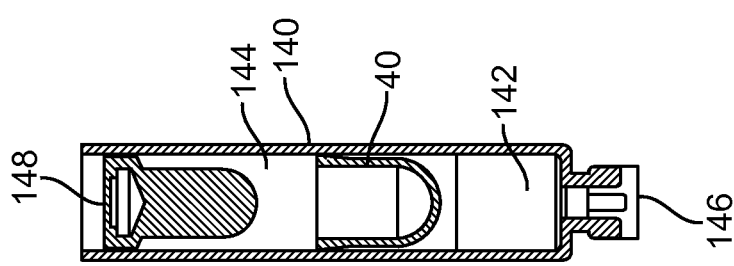
Figure 9A:
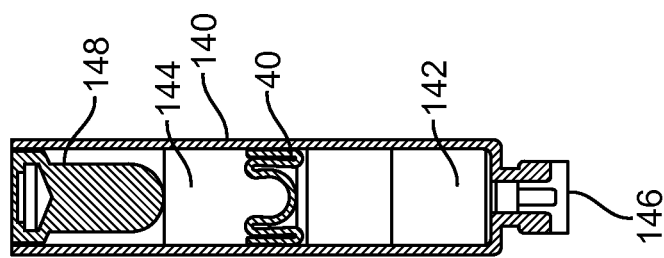
Figure 9H:
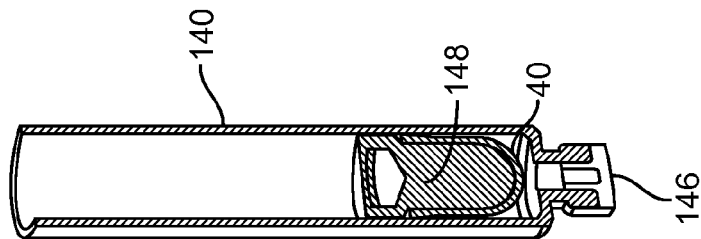
Figure 9G:
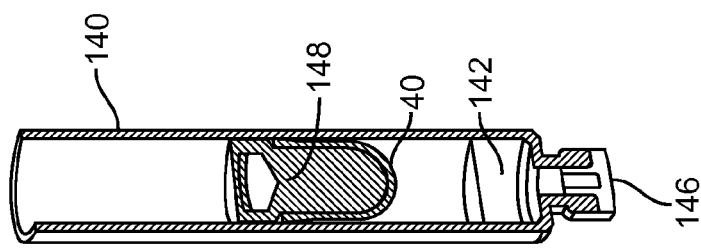
Figure 9F:
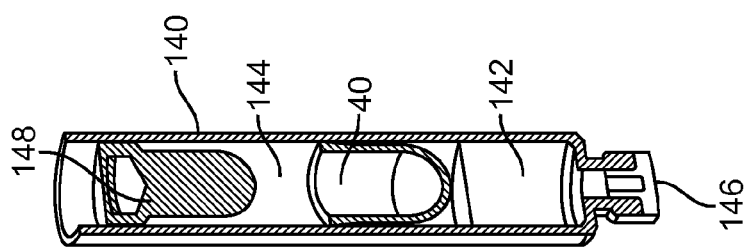
Figure 9E:
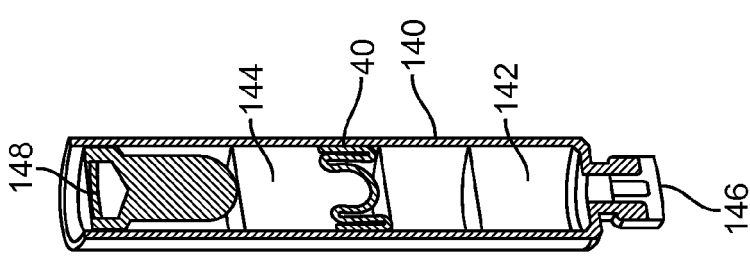

FIGS. 9A-9H illustrate use of reconstitution device 40 in a syringe 140. FIGS. 9E-9H are simply perspective views of the same steps shown in FIGS. 9A-9D, so the two sets of figures will only be described once, in reference to FIGS. 9A-9D. In FIG. 9A, reconstitution device 40 is disposed in syringe 140 in its first configuration, with deflection portion/cap 44 lodged in the locked position, and with a seal formed with the inner wall of syringe 140, thus forming two, separate compartments 142, 144 on either side of reconstitution device 40. Compartments 142, 144 may have any suitable form of substance located therein—i.e., fluid(s), solid(s) and/or gas (es)—according to various embodiments. Syringe 140 also includes a stopper 148 at one end and a medication exit port at an opposite end 146, where a needle might be attached. Reconstituted medication or other fluid generally exits through end 146, after reconstitution.

Referring to FIG. 9B, when stopper 148 is advanced through syringe 140, toward reconstitution device 40, the force generated in compartment 144 against reconstitution device 40 causes deflection portion 44 to deflect and thus dislodge, thus advancing the cap. As stopper 148 advances, the cap advances in the direction that stopper 148 moves. This configuration allows fluid to flow from compartment 144 to compartment 142, around reconstitution device 40. The force is generated, in this embodiment, by pushing against fluid (typically liquid with or without air) with stopper 148, thus compressing the fluid and generating pressure. As shown in FIG. 9C, the stopper 148 may be advanced farther through syringe 140 to meet with reconstitution device 40. In this embodiment, stopper 148 has a bullet-shaped profile, configured to mate with (i.e., fit within) reconstitution device 40 in the unlocked configuration. Finally, as illustrated in FIG. 9D, stopper 148 may be further advanced, along with reconstitution device 40, such that stopper 148 and reconstitution device 40 essentially act together as a plunger, causing the reconstituted medication to exit syringe 140 out of end 146. This is only one embodiment of a method for using reconstitution device 40. For example, in another embodiment, reconstitution device 40 may be used in a cartridge rather than syringe 140. In various embodiments, syringe 140 may be of any suitable size, and thus multiple different sizes of reconstitution device 40 may be provided, for use in the different variations of syringe 140. Furthermore, as suggested above, this or any alternative embodiment may be used to mix or reconstitute any substances or combinations of substances. Thus, no embodiments herein are limited to one particular use, medication, syringe, cartridge or the like.

FIGS. 10A-10C are perspective views of another alternative embodiment of a one-part reconstitution device 50, illustrating its use in a syringe 150, including a stopper 158 and a distal end 156, and in which reconstitution device 50 forms two, separate compartments 152, 154. Reconstitution device 50 may include two valves connected via an attachment therebetween. The attachment between the valves may make the fluid seal stronger and may make the valves pop in unison, although the attachment is not required. In other embodiments, more than two values in series may be used.

In FIG. 10A, reconstitution device 50 is disposed in syringe 150 in its first, locked configuration, with a seal formed with the inner wall of syringe 150, thus forming two, separate compartments 152, 154 on either side of reconstitution device 50. Compartments 152, 154 may have any suitable form of substance located therein—i.e., fluid(s), solid(s) and/or gas (es)—according to various embodiments. Referring to FIG. 10B, when stopper 158 is advanced through syringe 150, toward reconstitution device 50, the force generated in compartment 154 against reconstitution device 50 causes reconstitution device 50 to pop open to a second, unlocked configuration to allow fluid flow past it. The force is generated, in this embodiment, by pushing against fluid (typically liquid with or without air) with stopper 158, thus compressing the fluid and generating pressure. As shown in FIG. 10C, the stopper 158 may be advanced farther through syringe 150 to meet with reconstitution device 50, so that stopper 158 and reconstitution device 50 essentially act together as a plunger, causing the reconstituted medication to exit syringe 150 out of end 156. This is only one embodiment of a method for using reconstitution device 50. For example, in another embodiment, reconstitution device 50 may be used in a cartridge rather than syringe 150. In various embodiments, syringe 150 may be of any suitable size, and thus multiple different sizes of reconstitution device 50 may be provided, for use in the different variations of syringe 150. Furthermore, as suggested above, this or any alternative embodiment may be used to mix or reconstitute any substances or combinations of substances. Thus, no embodiments herein are limited to one particular use, medication, syringe, cartridge or the like.

FIGS. 11A-11D are cross-sectional views (FIGS. 11A and 11C) and perspective views (FIGS. 11B and 11D) of yet another alternative embodiment of a reconstitution device 60. In this embodiment, reconstitution device 60 has a mechanism of action similar to that of reconstitution device 30, described in relation to FIGS. 6A-6G. Reconstitution device 60 includes an outer, contact portion 62, including two circumferential ribs 63, an inner, deflection portion 64, including multiple apertures 65 (or "perforations"), and a peg 68 (or "plug") coupled with the deflection portion 64. Deflection portion 64, in communication with peg 68, rolls forward to enable peg 68 to dislodge. Apertures 65 allow for fluid communication through reconstitution device 60. Similar to the previously described embodiments, reconstitution device 60 is a one-part device. In use, deflection portion 64 moves between a first configuration, in which peg 68 and deflection portion 64 block fluid flow and help maintain the sealed separation between two compartments of a cartridge or syringe, and a second configuration, in which deflection portion 64 flips open to a straighter form, thus moving peg 68 forward out of the locked position and allowing fluid to flow through apertures 65 for reconstitution of the substance.

Figure 11B:
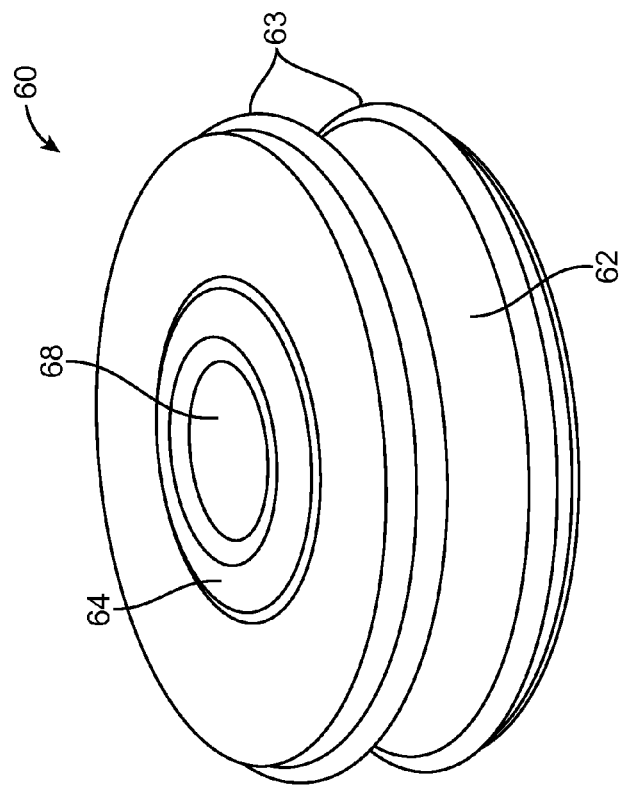
FIGS. 11A-11D are various views of a one-part reconstitution device having a peg that in a first position blocks fluid flow through the center of the device, according to another alternative embodiment.
Figure 11A:
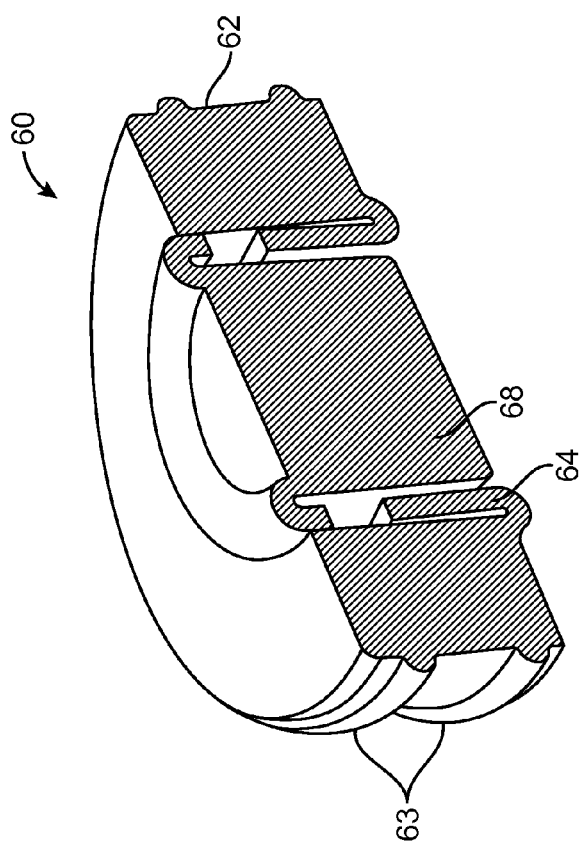
Figure 11D:
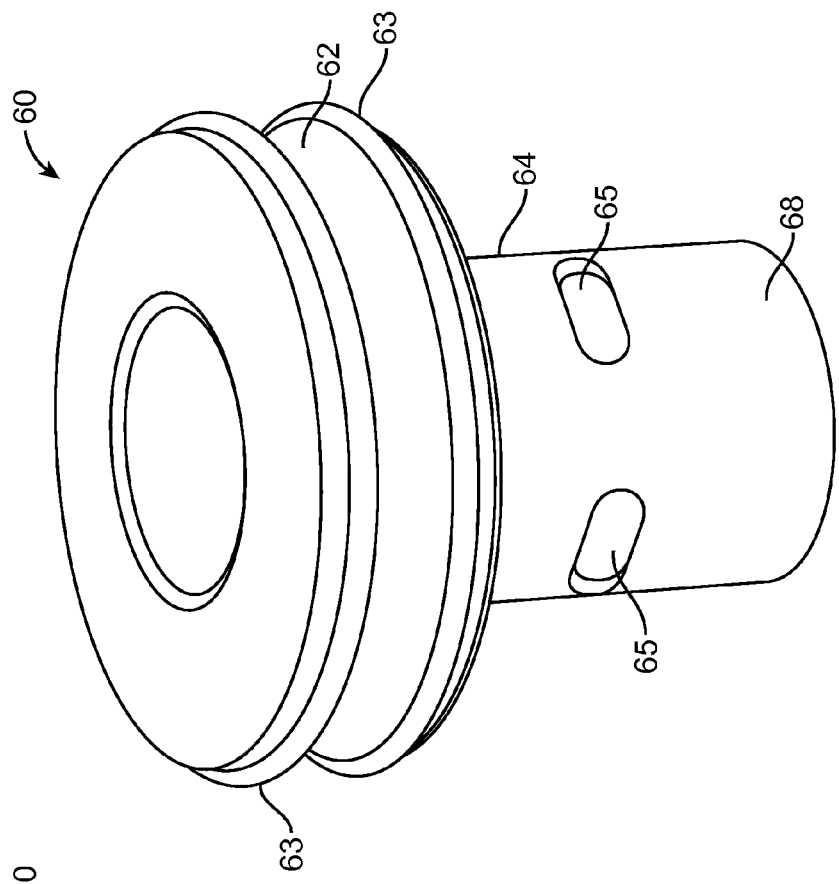
Figure 11C:
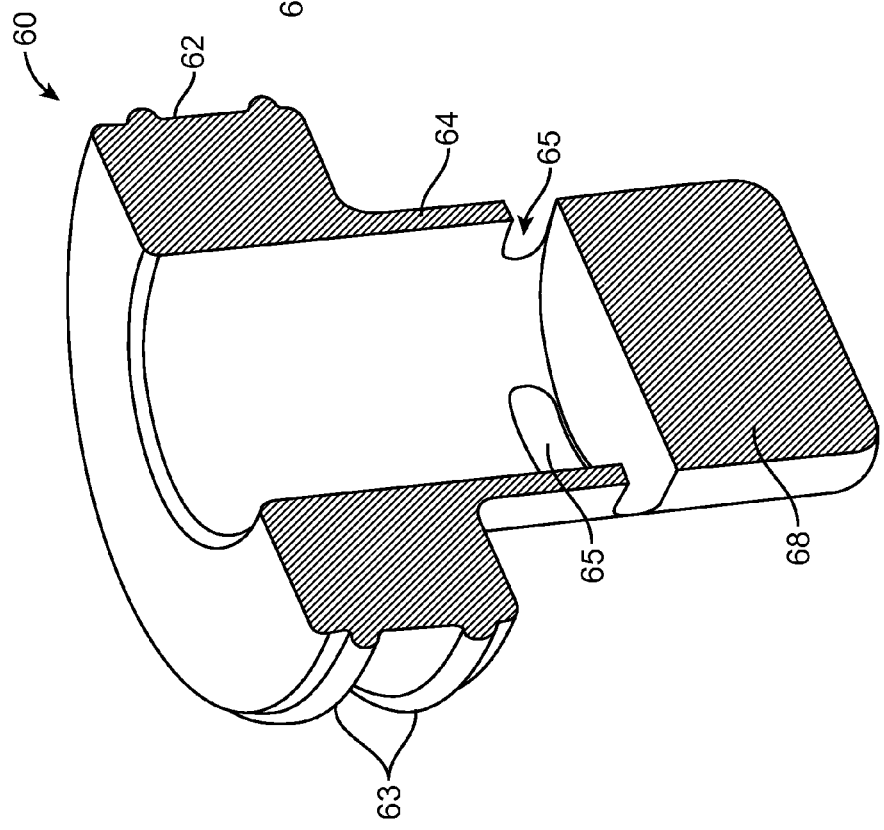

FIGS. 11A and 11B show reconstitution device 60 in the first, locked configuration, with peg 68 and deflection portion 64 configured to block fluid flow. FIGS. 11C and 11D show reconstitution device 60 with peg 68 and deflection portion 64 dislodged from the locked position and apertures 65 open to allow fluid flow. Ribs 63 may help reconstitution device 60 form a seal with an inner wall of a cartridge or syringe. As mentioned previously, reconstitution device 60 may be made of any suitable material.

Figure 12A:
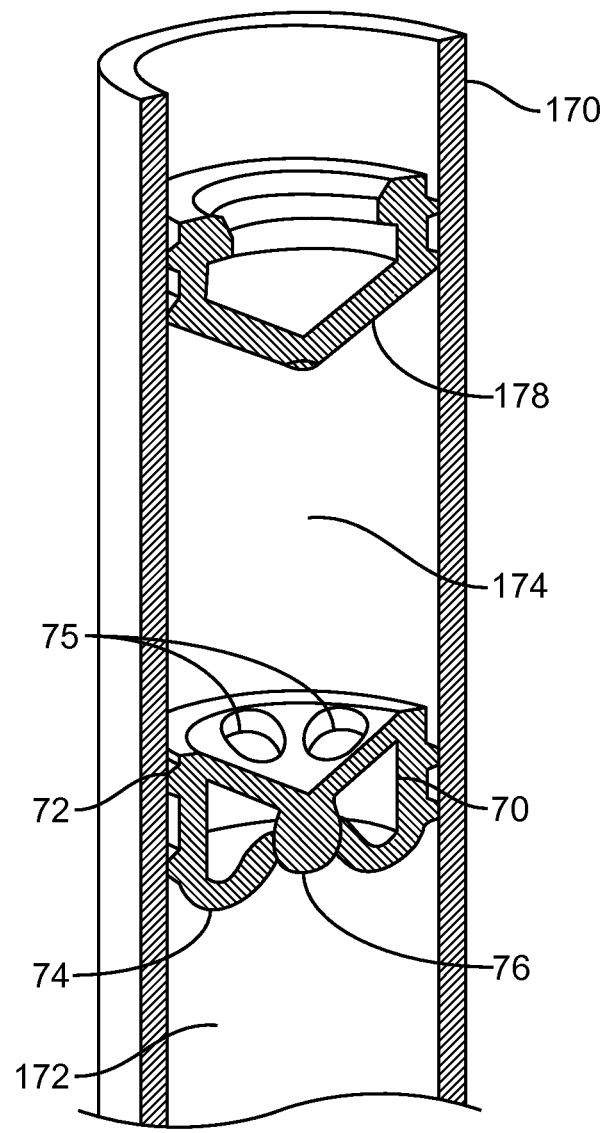
FIGS. 12A-12C are perspective views of a syringe with a one-part reconstitution device having a disc with a hole that is plugged with a rounded peg, according to another alternative embodiment.
Figure 12B:
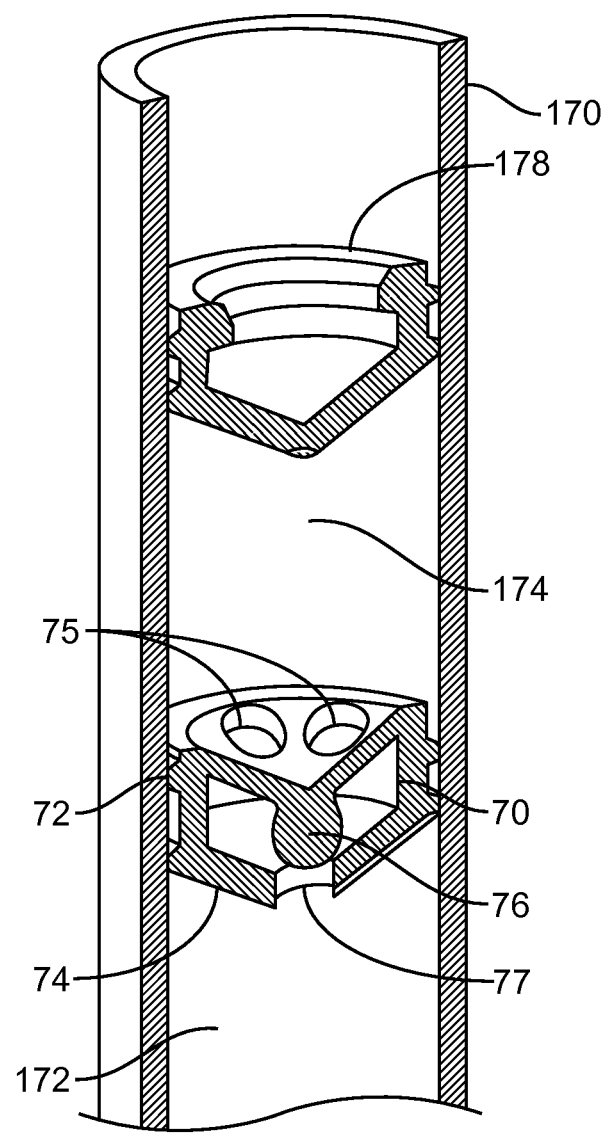
Figure 12C:
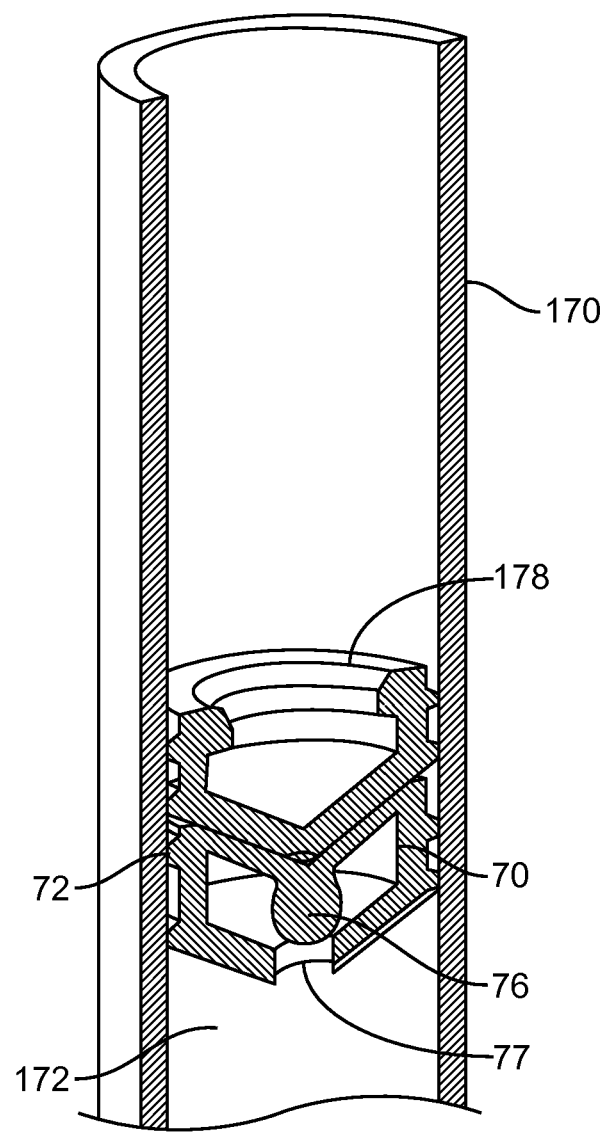

FIGS. 12A-12C are perspective views of another alternative embodiment of a one-part reconstitution device 70, illustrating its use in a syringe 170. Only a portion of syringe 170 is shown, including a stopper 178 and two compartments 172, 174 formed by reconstitution device 70. Reconstitution device 70 may include a contact portion 72, a deflection portion 74, including a hole 77, a rounded peg 76 and multiple additional holes 75. Hole 77 and additional holes 75 allow fluid to flow through reconstitution device 70 when it is in an open configuration.

In FIG. 12A, reconstitution device 70 is disposed in syringe 170 in its first, locked configuration, with peg 76 blocking hole 77 and a seal formed with the inner wall of syringe 170, thus forming compartments 172, 174 on either side of reconstitution device 70. Compartments 172, 174 may have any suitable form of substance located therein—i.e., fluid(s), solid(s) and/or gas(es)—according to various embodiments. Referring to FIG. 12B, when stopper 178 is advanced through syringe 170, toward reconstitution device 70, the force generated in compartment 174 against reconstitution device 70 causes deflection portion 74 to advance and peg 76 to dislodge from hole 77, thus allowing fluid to flow through hole 77 and additional holes 75. The force is generated, in this embodiment, by pushing against fluid (typically liquid with or without air) with stopper 178, thus compressing the fluid and generating pressure. As shown in FIG. 12C, the stopper 178 may be advanced farther through syringe 170 to meet with reconstitution device 70, so that stopper 178 and reconstitution device 70 essentially act together as a plunger, causing the reconstituted medication to exit syringe 170 out of end 176. This is only one embodiment of a method for using reconstitution device 70. For example, in another embodiment, reconstitution device 70 may be used in a cartridge rather than syringe 170. In various embodiments, syringe 170 may be of any suitable size, and thus multiple different sizes of reconstitution device 70 may be provided, for use in the different variations of syringe 170. Furthermore, as suggested above, this or any alternative embodiment may be used to mix or reconstitute any substances or combinations of substances. Thus, no embodiments herein are limited to one particular use, medication, syringe, cartridge or the like.

Any one or more of the teachings, expressions, embodiments and examples described herein may be combined with any one or more of the other teachings, expressions, embodiments and examples. The above-described teachings, expressions, embodiments and examples should not, therefore, be viewed in isolation relative to each other. Various suitable ways in which the teaching herein may be combined or varied are intended to be included within the scope of the claims.

Having shown and described various embodiments of the present invention, further adaptations of the methods and systems described herein may be accomplished by appropriate modifications, without departing from the scope of the present invention. For instance, the examples, embodiments, geometrics, materials, dimensions, ratios, steps, and the like discussed above are illustrative and are not required. Accordingly, the scope of the present invention should be considered in terms of the following claims and should not to be limited to the details of structure and operation shown and described in the specification and drawings.

What is claimed is:

1. A one-part reconstitution device for temporarily separating two substances into two compartments within a cartridge or syringe and allowing for mixture of the two substances within the cartridge or syringe, the device comprising:
    an outer, contact portion configured to contact an inner surface of the cartridge or syringe; and
    an inner, deflection portion positioned within the contact portion, wherein the deflection portion is movable from a locked position, in which the deflection portion causes the contact portion to exert a first radial force against the inner surface, to an unlocked position, in which the deflection portion causes the contact portion to exert a second radial force against the inner surface, wherein the second radial force is less than the first radial force, and
    wherein movement of the deflection portion from a locked to an unlocked position allows the two substances in the two compartments to mix without piercing the deflection portion, and
    wherein the contact portion and the deflection portion comprise one part.

2. A device as in claim 1, wherein the cartridge or syringe defines a longitudinal axis, and wherein the deflection portion is configured to deflect in a distal direction along the longitudinal axis to move from the locked position to the unlocked position in response to pressure applied to a fluid in the cartridge or syringe proximal to the deflection portion.

3. A device as in claim 1, wherein the contact portion comprises an elastomeric ring.

4. A device as in claim 3, wherein the deflection portion comprises an elastomeric, dome-shaped portion within the ring.

5. A device as in claim 1, wherein the deflection portion changes from a convex shape to a concave shape upon moving from the locked position to the unlocked position.

6. A device as in claim 1, wherein an outer diameter of the contact portion is larger in the locked position than in the unlocked position.

7. A device as in claim 1, further comprising a plug attached to at least one of the contact portion or the deflection portion, wherein the deflection portion includes a hole, wherein the hole is plugged by the plug when the deflection portion is in the locked position, and wherein the hole is open and not plugged by the plug when the deflection portion is in the unlocked position.

8. A device as in claim 7, wherein the contact portion, the deflection portion and the plug comprise the one part.

9. A device as in claim 1, further comprising an outer ring attached to the contact portion, wherein the deflection portion in the locked position biases the outer ring against the cartridge or syringe, and wherein the deflection portion in the unlocked position radially retracts the outer ring.

10. A device as in claim 1, wherein the deflection portion defines a plurality of ridges and the ridges at least partially engage the inner surface of the cartridge or syringe when the deflection portion is in the unlocked position to allow fluid communication between the compartments.

11. A system for temporarily separating two substances within a syringe and allowing for mixture of the two substances within the syringe, the system comprising:
- a syringe; and
- a one-part reconstitution device configured to fit in the syringe, the reconstitution device comprising:
  - an outer, contact portion configured to contact an inner surface of the syringe; and
  - an inner, deflection portion positioned within the contact portion, wherein the deflection portion is movable from a locked position, in which the deflection portion causes the contact portion to exert a first radial force against the inner surface, to an unlocked position, in which the deflection portion causes the contact portion to exert a second radial force against the inner surface, wherein the second radial force is less than the first radial force,
- wherein movement of the deflection portion from a locked to an unlocked position allows the two substances to mix without piercing the deflection portion, and
- wherein the contact portion and the deflection portion comprise one part.

12. A system as in claim 11, wherein the deflection portion is configured to move from the locked position to the unlocked position without the reconstitution device moving through the syringe.

13. A system as in claim 11, wherein the deflection portion is configured to move from the locked position to the unlocked position while a plug of the reconstitution device remains stationary.

14. A system as in claim 11, wherein the syringe comprises a proximal end and a distal end, and wherein the deflection portion is configured to deflect in a distal direction, relative to the syringe, to move from the locked position to the unlocked position in response to pressure applied to a fluid in the syringe proximal to the deflection portion.

15. A system as in claim 11, further comprising a plunger driver configured to axially advance within the syringe, wherein the plunger driver is configured to urge the deflection portion from the locked position to the unlocked position.

16. A system as in claim 15, wherein the plunger driver is further configured to axially advance the reconstitution device longitudinally through the syringe.

17. A system as in claim 11, wherein the reconstitution device further comprises a plug attached to at least one of the contact portion or the deflection portion, wherein the deflection portion includes a hole, wherein the hole is plugged by the plug when the deflection portion is in the locked position, and wherein the hole is open and not plugged by the plug when the deflection portion is in the unlocked position.

18. A system as in claim 17, wherein the contact portion, the deflection portion and the plug comprise the one part.

19. A system as in claim 11, wherein the deflection portion defines a plurality of ridges and the ridges at least partially engage the inner surface of the syringe when the deflection portion is in the unlocked position to allow fluid communication between compartments of the syringe.

20. A system for temporarily separating two substances within a cartridge and allowing for mixture of the two substances within the cartridge, the system comprising:
- a cartridge; and
- a one-part reconstitution device configured to fit in the cartridge, the reconstitution device comprising:
  - an outer, contact portion configured to contact an inner surface of the cartridge; and
  - an inner, deflection portion positioned within the contact portion, the deflection portion defining a plurality of ridges and channels, wherein the deflection portion is movable from a locked position, in which the deflection portion causes the contact portion to exert a first radial force against the inner surface, to an unlocked position, in which the deflection portion causes the contact portion to exert a second radial force against the inner surface, wherein the second radial force is less than the first radial force,
- wherein the contact portion and the deflection portion comprise one part and movement of the deflection portion from a locked to an unlocked position allows the two substances to mix without piercing the deflection portion.

* * * * *